US011117946B2

(12) United States Patent
Loidl et al.

(10) Patent No.: US 11,117,946 B2
(45) Date of Patent: Sep. 14, 2021

(54) METHOD FOR PREPARING GLUCAGON-LIKE PEPTIDES (71) Applicant: BACHEM HOLDING AG, Bubendorf (CH)

(72) Inventors: Guenther Loidl, Rheinfelden (DE); Benjamin Neuhaus, Gempen (CH); Ralph O. Schoenleber, Lupsingen (CH); Andreas Stadelmaier, Muellheim (DE)

(73) Assignee: BACHEM HOLDING AG ( * ) Notice: Subject to any disclaimer, the term of this patent is extended or adjusted under 35 U.S.C. 154(b) by 63 days.

(21) Appl. No.: 16/086,460

(22) PCT Filed: Mar. 21, 2017

(86) PCT No.: PCT/EP2017/056664
§ 371 (c)(1),
(2) Date: Sep. 19, 2018

(87) PCT Pub. No.: WO2017/162650
PCT Pub. Date: Sep. 28, 2017

(65) Prior Publication Data
US 2019/0100569 A1 Apr. 4, 2019

(30) Foreign Application Priority Data
Mar. 23, 2016 (EP) .................................. 16162031

(51) Int. Cl.
A61K 38/04 (2006.01)
C07K 14/605 (2006.01)
C07K 1/04 (2006.01)
C07K 1/06 (2006.01)
C07K 1/08 (2006.01)
C07K 1/14 (2006.01)
A61K 38/00 (2006.01)

(52) U.S. Cl.
CPC ............ C07K 14/605 (2013.01); C07K 1/042 (2013.01); C07K 1/061 (2013.01); C07K 1/08 (2013.01); C07K 1/14 (2013.01); A61K 38/00 (2013.01)

(58) Field of Classification Search
None
See application file for complete search history.

(56) References Cited

U.S. PATENT DOCUMENTS

| 10,407,464 B2 * | 9/2019 | Bezemer .............. C07K 1/1075 |
| 2005/0165216 A1 | 7/2005 | Han et al. |
| 2010/0280221 A1 * | 11/2010 | Callens ................ C07K 1/1075 530/328 |
| 2012/0129768 A1 | 5/2012 | Wang et al. |
| 2012/0189627 A1 | 7/2012 | Heavner |
| 2015/0202317 A1 | 7/2015 | Rau et al. |

FOREIGN PATENT DOCUMENTS

| CN | 103145828 A | 6/2013 | |
| CN | 103275208 A | 9/2013 | |
| CN | 103275209 A | 9/2013 | |
| CN | 103980358 A | 8/2014 | |
| CN | 104045705 A | 9/2014 | |
| CN | 104045706 A | 9/2014 | |
| EP | 0 944 648 B1 | 3/2007 | |
| EP | 1 987 052 B1 | 4/2011 | |
| EP | 2 757 107 A1 | 7/2014 | |
| WO | 2007/090496 A1 | 8/2007 | |
| WO | 2011/134471 A1 | 11/2011 | |
| WO | 2012/171982 A1 | 12/2012 | |
| WO | 2012/171984 A1 | 12/2012 | |
| WO | 2012/171987 A1 | 12/2012 | |
| WO | 2014/199397 A2 | 12/2014 | |
| WO | WO-2014199397 A2 * | 12/2014 | |
| WO | 2015/028966 A2 | 3/2015 | |
| WO | 2015/154031 A1 | 10/2015 | |
| WO | 2016/005960 A1 | 1/2016 | |
| WO | WO-2016046753 A1 * | 3/2016 | ........... C07K 14/605 |
| WO | WO-2016067271 A1 * | 5/2016 | ........... C07K 14/605 |

OTHER PUBLICATIONS

International Preliminary Report on Patentability in International Application No. PCT/EP2017/056664, dated Oct. 4, 2018.
Written Opinion of the International Search Authority for PCT/EP2017/056664, dated Sep. 28, 2017.

* cited by examiner

Primary Examiner — Satyanarayana R Gudibande
(74) Attorney, Agent, or Firm — J.A. Lindeman & Co., PLLC (57) ABSTRACT

The present invention refers to a method for preparing a glucagon-like peptide, comprising precipitation of the peptide or of a precursor peptide by means of mixing with an anti-solvent comprising diisopropyl ether and acetonitrile. Further, the present invention also relates to a peptide conjugated to a solid phase and a pharmaceutical composition comprising a Liraglutide peptide obtainable from a method according to the present invention.

12 Claims, 2 Drawing Sheets

Specification includes a Sequence Listing.

Fig. 1

| | | |
|---|---|---|
| Glucagon | HSQGTFTSDYSKYLDSRRAQDFVQWLMN | (SEQ ID NO:1) |
| GLP-2 | HADGSFSDEMNTILDNLAARDFINWLIQTKITD | (SEQ ID NO:2) |
| GLP-1(7-37) | HAEGTFTSDVSSYLEGQAAKEFIAWLVKGRG | (SEQ ID NO:3) |
| Liraglutide | HAEGTFTSDVSSYLEGQAAKEFIAWLVRGRG | (SEQ ID NO:4) |
| Exendin 4 (1-39) | HGEGTFTSDLSKQMEEEAVRLFIEWLKNGGPSSGAPPPS-NH$_2$ | (SEQ ID NO:5) |
| Exenatide | HGEGTFTSDLSKQMEEEAVRLFIEWLKNGGPSSGAPPPS-NH$_2$ | (SEQ ID NO:6) |
| Lixisenatide | HGEGTFTSDLSKQMEEEAVRLFIEWLKNGGPSSGAPPSKKKKKK-NH$_2$ | (SEQ ID NO:7) |

Fig. 2

METHOD FOR PREPARING GLUCAGON-LIKE PEPTIDES

The present invention generally relates to the field of peptide synthesis at an industrial or laboratory scale. Improved methods for the preparation of glucagon-like peptides, in particular for the preparation of glucagon-like peptide 1 analogs, such as Liraglutide, are disclosed. The present invention is directed to methods of effectively preparing glucagon-like peptides, such as Liraglutide, and of isolating the crude peptide after synthesis.

In preferred embodiments, the present invention refers to a method for preparing a Liraglutide peptide, comprising precipitation of the Liraglutide peptide or of a precursor peptide by means of mixing it with an anti-solvent comprising diisopropyl ether and acetonitrile. Further, the present invention relates to a Liraglutide peptide precursor, which is conjugated to a solid phase, and to a pharmaceutical composition comprising a Liraglutide peptide obtainable from a method according to the present invention.

The human GCG gene (HGNC:4191) encodes multiple related peptides including glucagon, glucagon-like peptide 1 (GLP-1) and glucagon-like peptide 2 (GLP-2). These share considerable sequence homology (cf. FIG. 1) and are involved in controlling blood glucose homeostasis, intestinal cell proliferation, and satiety. The forms of GLP-1 known to be biologically active, GLP-1 (7-37) and GLP-1 (7-36) amide, exert their effects via activation of the GLP-1 receptor. Amongst other physiological functions, GLP-1 is a potent glucose-dependent insulin tropic hormone, strongly inhibits glucagon secretion, has protective and proliferative effects on the beta cells of the pancreatic islets, and inhibits gastrointestinal secretion and motility. Abnormal GLP-1 function has been implicated in obesity, postprandial reactive hypoglycemia, and type 2 diabetes. Hence, GLP-1 analogs are of considerable interest in pharmaceutical research.

Variants and derivatives of the peptide hormone exendin-4 found in Gila monster (*Heloderma suspectum*) as well as variants and derivatives of the GLP-1 peptide itself are being extensively studied.

Marketed drug compounds comprise Exenatide and Lixisenatide, both derived from the exendin-4 peptide, as well as the GLP-1 derived Liraglutide. Liraglutide (N-ε-(γ-Glu (N-α-hexadecanoyl)))-$Lys^{26}Arg^{34}$-GLP-1(7-37), also known as NN2211, has been approved for the treatment of type 2 diabetes and for the treatment of obesity in adults with related comorbidity. The compound is being produced at an industrial scale by semi-synthetic techniques. EP-B 0 944 648 describes reacting a recombinantly expressed parent peptide with $N^{\alpha}$-hexadecanoyl-Glu(ONSu)-OtBu to obtain Liraglutide (cf. Example 35 thereof).

It is however desirable to provide better methods for the large scale preparation, full chemical synthesis of glucagon-like peptides such as Liraglutide.

Chemical peptide synthesis in general is well-known in the art (cf., brochure "Solid Phase Peptide Synthesis Bachem—Pioneering Partner for Peptides", published by Global Marketing, Bachem group, June 2014). During synthesis, formation of the peptide bond between the alpha amino group of a first amino acid and the alpha carboxyl group of a second amino acid should be favored over unintended side reactions. This is commonly achieved by the use of "permanent" and "temporary" protecting groups. The former are used to block, e.g., reactive amino acid side chains and the C-terminal carboxyl group of the growing peptide chain and are only removed at the end of the entire synthesis. The latter are used to block, e.g., the alpha amino group of the second amino acid during the coupling step, thereby avoiding, e.g., peptide bond formation between multiple copies of the second amino acid. Two standard approaches to chemical peptide synthesis can be distinguished, namely Liquid Phase Peptide Synthesis (LPPS) and Solid Phase Peptide Synthesis (SPPS).

LPPS, also referred to as Solution Peptide Synthesis, takes place in a homogenous reaction medium. Successive couplings yield the desired peptide. Virtually no standard protocol exists and careful planning is required to select from a variety of possible protecting group combinations, coupling methods, and solvents. LPPS usually involves the isolation, characterization, and—where desired—purification of intermediates after each coupling. Longer peptides are commonly synthesized by convergent approaches, where several fragments are assembled in parallel and finally combined to yield the end product.

In standard SPPS, a peptide anchored by its C-terminus to an insoluble polymer resin is assembled by the successive addition of the protected amino acids constituting its sequence, i.e. the synthesis proceeds from the peptide's C-terminus to the N-terminus. Successive cycles of amino acid addition are carried out, each consisting of: a) cleavage of the Nα-protecting group from the resin-bound peptide, b) washing steps, c) coupling of a protected amino acid, and d) washing steps. Because the growing chain is bound to the insoluble support, the excess of reagents and soluble by-products can be removed by simple filtration. Washing steps with appropriate solvents ensure the complete removal of cleavage agents after the deprotection step a) as well as the elimination of excesses of reagents and soluble by-products resulting from the coupling step c). At the end of the synthesis, the peptide is cleaved from the resin and protecting groups are removed (cf., brochure "Solid Phase Peptide Synthesis Bachem—Pioneering Partner for Peptides", published by Global Marketing, Bachem group, June 2014). The so-called Fmoc SPPS relies on the use of 9-fluorenylmethyloxycarbonyl (Fmoc) as the temporary amino protecting group and is the most popular form of SPPS. Contrary to LPPS, peptide purification can only be performed at the end of the synthesis, after cleavage from the resin. This is often disadvantageous in particular for the synthesis of large peptides, where various, resin-bound side products can accumulate in addition to side products formed during deprotection or due to degradation. As a result, the purification of the final product may be very challenging. When developing an SPPS process for industrial manufacture, it is therefore imperative to optimize the purity of the crude peptide product.

In addition to LPPS and SPPS, hybrid approaches can be utilized, where fragments are first synthesized by one of the above techniques and then joined together using the other approach. This strategy is typically employed for large peptides with challenging sequences. The above approaches have in common that a final and/or intermediate peptide product needs to be recovered from a solution. Depending on the synthesis strategy chosen, the additional components of said peptide solution may vary, and often comprise a cleavage composition containing TFA and scavengers.

The standard method for peptide isolation after TFA cleavage is the so-called cold ether workup: The peptide solution is mixed with cold ether as an anti-solvent to cause peptide precipitation, and the precipitate is collected by filtration and/or centrifugation.

Diethyl ether, diisopropyl ether, or methyl tert. butyl ether (MTBE) are routinely used for this purpose. When the anti-solvent is added to the peptide solution, this is referred to as a "classical" precipitation protocol; when the peptide solution is added into the anti-solvent, this is referred to as "inverse" precipitation protocol.

The nature of the precipitate typically has some impact in laboratory and industrial manufacture, because it influences the quality of the crude peptide as well as further processing: Ideally, precipitation is nearly complete, but related impurities are decreased and TFA content is low. Moreover, efficient filtering requires precipitates of a suitable consistency and particle size to avoid clogging of the filter or loss of material sticking to vessel walls.

Although it has previously been recognized that the precipitation scheme may improve purity and handling of the crude peptide (US 2005/0165216), surprisingly little attention has been given to the details of this step.

Documents CN-A 103275209, CN-A 103275208, CN-A 104045706, CN-A 104045705, CN-A 103145828, CN-A 103980358, and EP-A 2 757 107, disclose SPPS or hybrid approaches for the synthesis of Liraglutide. In each case, crude Liraglutide is precipitated from a solution comprising TFA and scavengers using cold diethyl ether as an anti-solvent.

WO 2014/199397 and WO 2016/005960 disclose SPPS and/or hybrid approaches for the synthesis of Liraglutide. The crude Liraglutide is precipitated from a solution comprising TFA and scavengers using cold MTBE or diisopropyl ether as an anti-solvent.

EP-B 1 987 052 discloses an SPPS approach for the synthesis of glucagon-like peptides, where the crude peptide is precipitated from a solution comprising TFA and scavengers using cold MTBE.

US-A 2005/0165216 teaches the use of alcohols having three or more carbon atoms for precipitation of peptides.

WO 2012/171984, WO 2012/171982, and WO 2012/171987 deal with the problems encountered during precipitation of peptides prepared by LPPS.

It is taught that direct precipitation out of the polar, aprotic solvents used in LPPS results in the formation of sticky, gum-like precipitates. This can be avoided by first extracting a peptide of interest into 2-methyltetrahydrofuran or toluene, followed by precipitation of the peptide from this phase. Acetonitrile, diethyl ether, diisopropyl ether, n-heptane and toluene are indicated as suitable anti-solvents for inducing peptide precipitation from the extract.

Precipitation with mixtures of acetonitrile and diisopropyl ether has been described in rare cases for the preparation of short-length peptides. US 2010/0280221 describes the preparation of an octapeptide (length: 8 amino acids) by LPPS. The procedure involves peptide precipitation from acetic acid/dioxane by acetonitrile/diisopropyl ether at ambient temperature. WO 2015/154031 describes a method of precipitating AMG 614, a highly polar, artificial peptidic compound consisting of seven D-amino acids and a disulfide bonded single L-Cys, by a mixture of acetonitrile and diisopropyl ether.

In the view of the prior art, there was still the need for improving the method of preparation of larger size peptides, such as glucagon-like peptides, like Liraglutide. In particular, the synthesis and purification of the crude peptide products needed optimization so as to obtain crude peptide products of improved purity and with improved macroscopic properties. The present inventors have developed improved methods for the synthesis and precipitation of a crude Liraglutide peptide, which can be used at an industrial scale.

Surprisingly, it has been found that larger size peptides such as glucagon-like peptides, like Liraglutide, can be particularly well precipitated by means of anti-solvents comprising diisopropyl ether and acetonitrile, in particular when used in a (diisopropyl ether:acetonitrile) volume ratio of from (3:1) to (10:1).

In general terms, an aspect of the present invention therefore relates to a method for preparing a glucagon-like peptide or a salt thereof, comprising the steps:
(i) providing a solution S comprising the crude glucagon-like peptide
(ii) precipitation of the peptide of step (i) by means of mixing it with an anti-solvent comprising diisopropyl ether and acetonitrile, wherein the volume ratio (diisopropyl ether:acetonitrile) is in the range of from (3:1) to (10:1); and
(iii) isolating the precipitate obtained from step (ii), preferably by means of filtration and/or centrifugation.

The present invention provides, in one aspect, a method for the preparation of a glucagon-like peptide, comprising:
(i) obtaining a solution comprising the glucagon-like peptide; and
(ii) precipitation of the glucagon-like peptide, using an anti-solvent comprising diisopropyl ether and acetonitrile and in a ratio selected from the range of (3:1) v/v to (10:1) v/v; and
(iii) separation of the precipitate.

One embodiment of the present invention refers to a method for preparing a Liraglutide peptide or a salt thereof, comprising:
(i) providing a solution S comprising a peptide of formula I:

His-Ala-Glu-Gly-Thr-Phe-Thr-Ser-Asp-Val-Ser-Ser-
Tyr-Leu-Glu-Gly-Gln-Ala-Ala-B$^1$-Glu-Phe-Ile-Ala-
Trp-Leu-Val-Arg-Gly-Arg-Gly, wherein B$^1$ is Lys(palmitoyl-Glu-OH) or Lys(H-Glu-OH);
(ii) precipitation of the peptide of step (i) by means of mixing solution S with an anti-solvent comprising diisopropyl ether and acetonitrile, wherein the volume ratio (diisopropyl ether:acetonitrile) is in the range of from (3:1) to (10:1); and
(iii) isolating the precipitate obtained from step (ii), preferably by means of filtration and/or centrifugation.

The person skilled in the art will notice that formula I also embraces salts of the polypeptide strand depicted above. It will be understood by a person skilled in the art that a peptide as used herein may optionally bear any counter ions known in the art, such as anions or cations, such as e.g., chloride ions, acetate ions, carbonate ions, hydrocarbonate ions, sodium ions, potassium ions, magnesium ions, any ions of the cleavage solution (e.g., TFA ions, bromide ions, perchlorate ions, ammonium ions) and/or cations or anions of residuals of protecting groups. Further, a peptide may optionally be covalently or non-covalently associated to traces of one or more scavengers, such as, e.g., triisopropylsilane (TIPS), dithiothreitol (DTT), dithioerythriol (DTE), anisole, thioanisole or 1,2-ethanedithiol. The methods of the present invention may advantageously be used to improve handling, yield, and/or purity of a crude glucagon-like peptide, in particular Liraglutide, in particular for methods of large-scale preparation. Particularly beneficial is a method comprising SPPS of a precursor of a glucagon-like peptide, cleaving said precursor off the resin to obtain the crude glucagon-like peptide in the cleavage composition and separating the cleaved crude glucagon-like peptide from the cleavage composition.

In general, several abbreviations and definitions are used throughout the present invention:
Abbreviations:
Boc tert. Butyloxycarbonyl
CLEAR cross-linked ethoxylate acrylate
DBU diazabicyclo[5.4.0]undec-7-ene
DEPBT 3-(diethoxy-phosphoryloxy)-3H-benzo[d][1,2,3]triazin-4-one
DIC diisopropylcarbodiimide
DIPEA diisopropylethylamine
Dmb 2,4-dimethoxybenzyl
DMF N,N-dimethylformamide
DTE 1,4-dithioerythriol
DTT 1,4-dithiothreitol
EDT 1,2-ethanedithiol
Fmoc 9-fluorenylmethyloxycarbonyl
Hmb 2-hydroxy-4-methoxybenzyl
HOBt hydroxybenzotriazole
HPLC High Performance Liquid Chromatography
The term HPLC as used herein includes UHPLC.
IPE diisopropyl ether
LPPS Liquid Phase Peptide Synthesis
MALDI-MS Matrix-Assisted Laser Desorption Ionization Mass Spectrometry
MTBE methyl tert. butyl ether
MTT 4-methyltrityl
NMP N-methylpyrrolidone
OMpe 3-methylpent-3-yl ester
OtBu tert. butyl ester
ONSu=OSu N-hydroxysuccinimide
OXYMAPURE® cyano-hydroxyimino-acetic acid ethyl ester
PEG polyethylene glycol
PEGA acrylamide-PEG co-polymer
Pbf 2,2,4,6,7-Pentamethyldihydrobenzofurane-5-sulfonyl
RT room temperature
SPPS Solid Phase Peptide Synthesis
tBu tert. butyl
TBTU (benzotriazolyl)tetramethyluronium tetrafluoroborate
TES triethylsilane
THF tetrahydrofuran
TIPS triisopropylsilane
Trt trityl
TFA trifluoroacetic acid
UHPLC Ultra High Performance Liquid Chromatography Unless indicated otherwise, liquid mixtures are defined by volume percentages and volume ratios.

As used herein, the term "peptide" and "polypeptide" may be understood interchangeably.

Unless indicated otherwise, peptide sequences are indicated herein starting with the N-terminus (left) and ending with the C-terminus (right). Table 1 illustrates different notations, which are equivalent and will be used interchangeably throughout this document.

Amino acids will be referred to interchangeably by either their full name (exemplified: alanine), 3-letter code according to WIPO Standard ST. 25 (e.g. Ala), or 1-letter code (e.g. A). As far as the enantiomeric form is not expressly specified, L-amino acids are in general referred to.

It should be noted, however, that the present invention can likewise be put to practice using D-amino acids and other stereoisomers.

TABLE 1

Notation of peptides

| Notation | Explanation |
| --- | --- |
| H-Gly-Leu-Ala-OH | This notation stresses that the N-terminal amino group ("H") and C-terminal carboxyl ("OH") group are not modified. |
| Gly-Leu-Ala | Terminal groups are only expressly stated if they are modified. |
| GLA | 1-letter code. Terminal groups are only expressly stated if they are modified. |
| Glycyl-L-leucyl-L-alanine | "written out in full" |

The following, widely accepted notation will be used for amino acid derivatives: Substituents at the alpha amino group ($N^\alpha$) are indicated to the left of the amino acid symbol and separated by a hyphen, substituents at the alpha carboxy group are indicated to the right of the amino acid symbol and separated by a hyphen, substituents at the side chain are indicated in brackets immediately to the right of the amino acid symbol. For unmodified alpha-amino acids, the substituent at the alpha amino group ($N^\alpha$) is a proton (H—) and the substituent at the alpha carboxy group is a hydroxyl (—OH)

For branched dipeptides, this notation is adhered to in a nested format. For example, Fmoc-Lys(Boc-Glu-OtBu)-OH refers to a Lys derivative with a Fmoc protected alpha amino group and a free alpha carboxyl group, whose side chain is substituted with a glutamyl moiety having a Boc protected alpha amino group and an OtBu protected carboxyl group. The glutamyl moiety forms an amide bond to the Lys side chain via its gamma carboxyl group.

The analogous notation is used for substituted amino acids, which are part of a peptide. For example, Aaa1-Aaa2-Lys(Boc-Glu-OtBu)-Aaa4-Aaa5 refers to a branched pentapeptide, where the Lys side chain at position 3 is substituted with a amide bonded glutamyl moiety having a Boc protected alpha amino group and an OtBu protected carboxyl group. Hence, said amide bond is between the Lys' epsilon amino group and the Glu's gamma carboxyl group.

As a further example of a substituted amino acid, which is part of a peptide, the expression Lys(palmitoyl-Glu-OH) refers to a Lys moiety, which is incorporated into a peptide and to whose epsilon amino group ($N^\epsilon$), i.e. side chain, a palmitoyl-Glu moiety is bound via its gamma carboxyl group ($C^\gamma$), thereby forming an amide bond between the $N^\epsilon$ of the Lys and the $C^\gamma$ of the Glu. In the palmitoyl-Glu moiety, the palmitoyl residue is bound to the alpha amino group (Na) of the Glu. The moiety Lys(palmitoyl-Glu-OH) may also be designated as Lys(hexadecanoyl-Glu-OH), Lys(N-ε-(γ-Glu-($N^\alpha$-hexadecanoyl))) or Lys($N^\epsilon$-(γ-glutamyl-($N^\alpha$-hexadecanoyl))).

As yet another example, the moiety Lys(H-Glu-OH) refers, in the context of a peptide sequence, to a Lys moiety to whose epsilon amino group ($N^\epsilon$) an unprotected Glu moiety is bound via its gamma carboxyl group ($C^\gamma$), thereby forming an amide bond between the $N^\epsilon$ of the Lys and the $C^\gamma$ of the Glu. In the Glu moiety, the alpha amino group ($N^\alpha$) is free. The moiety Lys(H-Glu-OH) may also be designated as Lys(N-ε-(γ-Glu(H)-OH), Lys(N-ε-(γ-Glu-OH) or Lys($N^\epsilon$-(γ-glutamyl-OH).

The person skilled in the art will immediately notice that the peptide of formula I refers to a derivative of the plain Liraglutide polypeptide strand, written in one-letter code:

(SEQ ID NO: 4)
HAEGTFTSDVSSYLEGQAAKEFIAWLVRGRG, wherein the lysyl moiety in position 20 of the amino acid sequence ($Lys^{20}$, $K^{20}$) is modified. More in detail, the epsilon amino group of the $Lys^{20}$ is conjugated to the gamma carboxyl residue of a glutamyl moiety (γ-Glu, γ-E) via an amide bond. This glutamyl moiety will typically bear a free alpha carboxyl group. The glutamyl moiety may either be conjugated to a palmitic acid=hexadecanoic acid moiety via its amino group, or may bear a free —$NH_2$ (alpha amino group, $N^α$).

Preferably, the peptide of formula I is (essentially) free of any protecting groups and has no other modifications at amino acid side chains except the moiety of $Lys^{20}$. Accordingly, the peptide of formula I is preferably the fully unprotected peptide, which is preferably not further modified.

Alternatively, the N-terminus of the peptide of formula I may be modified (e.g., acylated (e.g., acetylated)). Alternatively or additionally, the C-terminus may be modified (e.g., amidated).

Alternatively or additionally, one or more amino acid moiety side chains may be conjugated with a fluorophore. Optionally, the peptide of formula I may also be labeled radioactively (e.g., by $^3H$, $^{32}P$, $^{35}S$, $^{14}C$, $^{99m}Tc$ or lanthanides (e.g., $^{64}Gd$)) or may be labelled with a spin label, such as one or more heavy isotopes, e.g., $^{13}C$, detectable by Nuclear Magnetic Resonance (NMR).

The glucagon-like peptide comprised in the solution of step (i) will typically consist of natural L-amino acids. However, alternatively, the peptide may also comprise one or more non-natural amino acid(s) such as, e.g., D-amino acid(s), beta amino acid(s), methylated amino acid(s) (e.g., N-methylated amino acid(s)) or may even consist of such.

The person skilled in the art will notice that in a polar environment, in particular in an aqueous environment, the peptide strand of the peptide of formula I or of any other glucagon-like peptide may form a salt such as, e.g., by means of binding protons or other cations and/or anions, releasing protons or other cations and/or anions at the termini and/or a some of the amino acid side chains.

Figure 1:
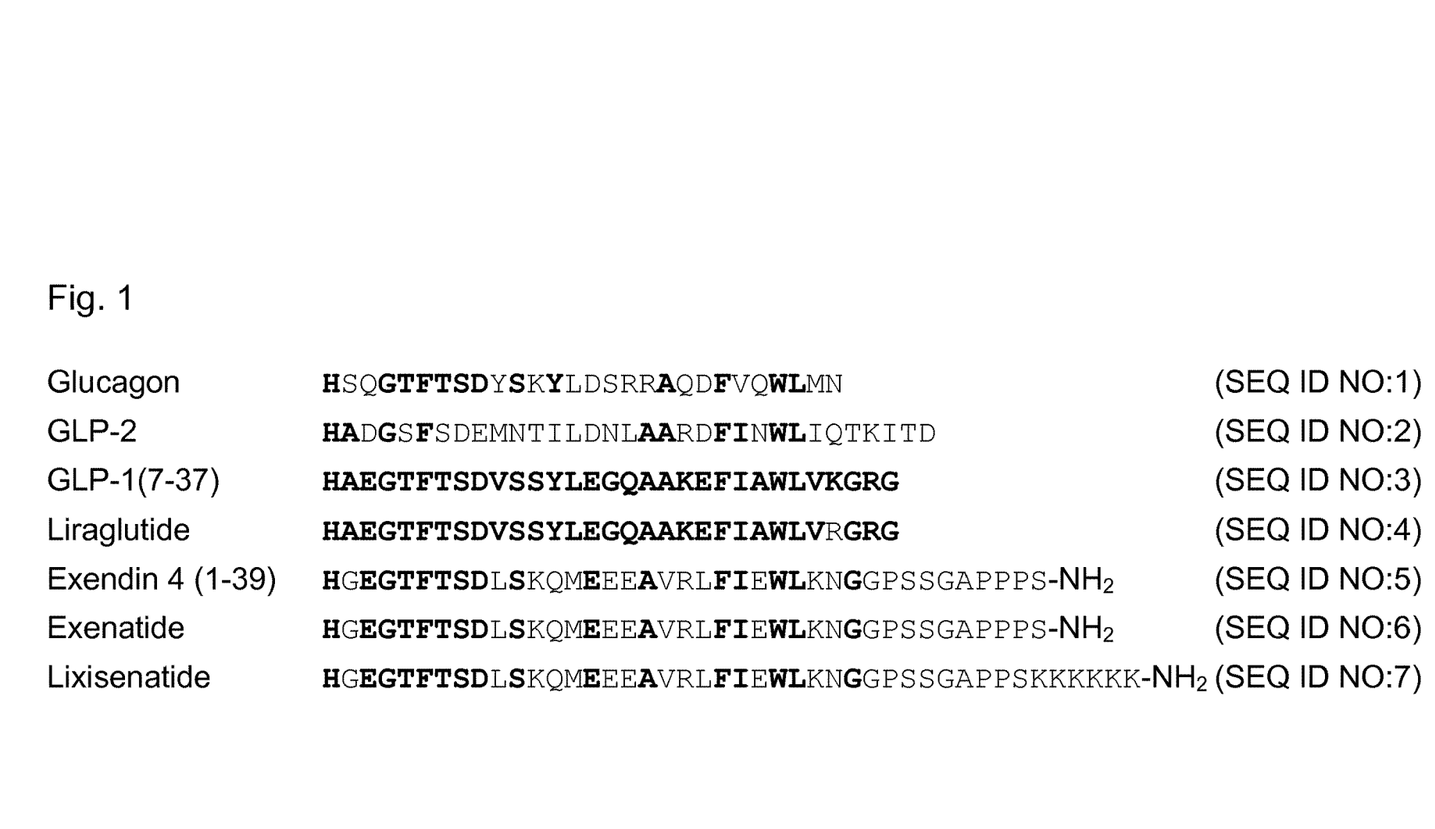
FIG. 1 shows the sequence alignment of selected glucagon-like peptides. Moieties sharing identity with the GLP-1 sequence are written in bold.

The term "glucagon-like peptide" or GLP as used herein refers to the homologous peptides derived from the GCG gene (HGNC:4191), the exendins and analogs thereof as well as derivatives of any of the foregoing. FIG. 1 depicts a sequence alignment of prototypical glucagon-like peptides.

The terms "glucagon-like peptide 1 analogs" and "GLP-1 analogs" are used herein interchangeably. As used herein, they relate to peptides capable of binding to the GLP-1 receptor. Derivatives and analogs of GLP-1 (7-37) and of exendin-4 (1-39) such as Exenatide, Lixisenatide, and Liraglutide are preferred GLP-1 analogs. Exemplarily, a GLP-1 analog may comprise a polypeptide strand having at least 80% homology to SEQ ID NO:4, more preferably a polypeptide strand having at least 90% homology to SEQ ID NO:4, in particular a polypeptide strand having at least 95% homology to SEQ ID NO:4 and, optionally, also a modification at the lysine moieties homolog to $Lys^{20}$ of SEQ ID NO:4. Homology as used herein is preferably sequence homology as determined over the entire length of SEQ ID NO:4.

As used herein, sequence homology may refer to any definition of sequence homology known in the art. In particular, sequence homology may be understood as sequence homology determined by BLAST (Basic Local Alignment Search Tool) of the National Center for Biotechnology Information (NCBI) in the version of the filing date of the present application.

The term "analog" or "analogs" as used herein refers to peptides whose sequence is derived from a first peptide sequence by replacement of up to 50% of the amino acid moieties, and/or by deletion of up to 10% of the amino acid moieties of said first peptide sequence, and/or by addition of up to 10 amino acid moieties.

Preferred analogs are derived from a first peptide sequence by replacement of up to 20% of the amino acid moieties, and/or by deletion of up to 10% of the amino acid moieties of said first peptide sequence, and/or by addition of up to 10 amino acid moieties.

The term "derivative" or "derivatives" as used herein refers to a compound which can be obtained from a first compound by a chemical reaction. As a result, a derivative may differ from the first compound by the presence or absence of substituents. For example, amino acid derivatives for use in SPPS usually differ from the amino acid they are derived from at least by the presence of an amino protecting group.

The term "providing a solution S comprising a peptide of formula I" may be understood in the broadest sense as obtaining any liquid composition containing a peptide of formula I. The peptide of formula I may be provided by any means known in the art. Exemplarily, it may be obtained from Solid Phase Peptide Synthesis (SPPS) or Liquid Phase Peptide Synthesis (LPPS) or a combination thereof. Alternatively, the plain polypeptide strand may also be obtained from a biotechnological method and the obtained polypeptide strand is modified by chemical/synthetic means subsequently.

Preferably, the peptide of formula I is obtained from SPPS, LPPS or a combination thereof. More preferably, the peptide of formula I is obtained from a method including or consisting of SPPS.

Typically, peptide synthesis (based on SPPS and LPPS) involves the use of various protecting groups and activated esters. Therefore, during the synthesis of the peptide of formula I, various protecting groups and activated esters may be used.

The term "protecting group" as used herein may be understood in the broadest sense as a group which is introduced into a molecule by chemical modification of a functional group to block said group from reaction in subsequent process steps, e.g. to prevent side reactions of the amino acid side chains. Examples of amino protecting groups are the Boc and Fmoc groups, examples of carboxylic acid protecting groups are unreactive esters such as methyl esters, benzyl esters, or tert. butyl esters.

In the context of the present invention, the term "activated ester" may be understood in the broadest sense as an ester which is suitable to spontaneously react with an amino group. Examples of activated esters are p-nitrophenyl, pentafluorophenyl and succinimido esters.

Although other means for obtaining a peptide of formula I, in particular other methods of synthesis, are also embraced by the scope of the present invention, the peptide of formula I is preferably obtained by Solid Phase Peptide Synthesis (SPPS). On the other hand, the methods of SPPS disclosed herein can also be used for the production of Liraglutide in combination with different peptide isolation schemes.

In SPPS, a precursor peptide of the peptide of formula I is synthesized on a resin (herein step (i-a)), i.e., on a "solid phase", most typically a bead-like structure which can be easily separated from liquid phase by filtration. Subsequent to synthesis of the resin-bound peptide, the peptide is released from the resin and protective groups are removed.

Accordingly, step (i) of the present invention may comprise the following steps
(i-a) providing a solid-phase conjugated glucagon-like peptide, wherein at least the side chains of Glu, Asp, and Lys carry protecting groups,
(i-b) cleavage of the peptide from the resin and, optionally, removal of protecting groups.

Therefore, in a preferred embodiment, step (i) of the method of the present invention comprises:
(i-a) providing a solid-phase conjugated glucagon-like peptide of the formula:

H-His-Ala-Glu-Gly-Thr-Phe-Thr-Ser-Asp-Val-Ser-Ser-Tyr-Leu-Glu-Gly-Gln-Ala-Ala-B²-Glu-Phe-Ile-Ala-Trp-Leu-Val-Arg-Gly-Arg-Gly-[resin], wherein $B^2$ is Lys (palmitoyl-Glu-OR$_1$) or $B^2$ is Lys (R$_2$-Glu-OR$_1$), with R$_1$ being a carboxylic acid protecting group and R$_2$ being an amino protecting group; and wherein at least the side chains of Glu, Asp, and Lys bear protecting groups; and
(i-b) cleaving the precursor peptide off the resin.

In preferred embodiments, $B^2$ is Lys(palmitoyl-Glu-OtBu) or Lys(Boc-Glu-OtBu). The moiety Lys(palmitoyl-Glu-OtBu) may also be designated as Lys(hexadecanoyl-Glu-OtBu).

As used herein, the terms "resin" and "[resin]" may be understood in the broadest sense as a bead-like structure usable for SPPS. The terms "resin", "solid phase" and "support" are used exchangeably herein.

SPPS is commonly carried out on gel phase rather than solid phase supports. Suitable resins may be based on polystyrene, polystyrene-PEG composites, PEG, PEGA, cross-linked ethoxylate acrylate (CLEAR), polyamides, polydimethylacrylamide, or any other support with the desired physical and chemical properties. Resins based on beaded polystyrene with 1% divinylbenzene are among the routinely used supports, typically having a size distribution of 200-400 mesh or 100-200 mesh. Polystyrene based 4-Alkoxybenzyl alcohol (Wang) resin, diphenyldiazomethane (PDDM) resin, 4-(2',4'-Dimethoxyphenyl-Fmoc-aminomethyl)-phenoxymethyl-polystyrene (Rink) resin, 2-Methoxy-4-alkoxybenzyl alcohol (Sasrin) resin, and especially 2-Chlorotrityl chloride (CTC) resin are particularly suitable for use with the methods of the present invention and are commercially available from suppliers such as Sigma-Aldrich, Bachem and EMD Millipore. However, any other resin suitable for SPPS may be used.

As an alternative to immobilization via the C-terminal carboxyl group, the peptide may also be conjugated to the resin via a side chain of a (preferably terminal) amino acid.

As a further alternative, the peptide may also be conjugated to the resin via the N-Terminus and synthesized from the N- to the C-terminus (inverse peptide synthesis).

The person skilled in the art will be aware of a large variety of SPPS methods. In general, any type of SPPS may be used in the context of the present invention.

Various types of equipment can be used for SPPS. Manual, semi-automated and automated synthesizers for either batchwise or continuous flow SPPS are available. For any given equipment, the resin may be chosen properly so as to meet the mechanical requirements imposed by the equipment.

The person skilled in the art is well aware of the fact that resin load may influence effectivity in SPPS, in particular in industrial SPPS. This may have particular impact when dealing with long, aggregation-prone peptide sequences such as the glucagon-like peptides: On one side, process efficiency increases with increasing resin load. On the other side, it is essential to reduce on-resin precipitation by reducing resin load. Hence, a delicate balance may be met and the optimal resin load can be established by routine experimentation for any given SPPS protocol. Resin load can be varied, e.g., either by using resins for which different substitution degrees are commercially available, or by coupling the second amino acid in molar deficit relative to the first amino acid, and subsequently acetylating, i.e. blocking, unreacted first amino acids. Likewise, the first amino acid may be coupled in molar deficit to the resin, followed by a blocking step. In preferred embodiments of the present invention, a resin load in the range of around 0.2 mmol/g to around 0.9 mmol/g is used, for example around 0.2 mmol/g, 0.3 mmol/g, 0.4 mmol/g, 0.5 mol/g, 0.6 mmol/g, 0.7 mmol/g, 0.8 mmol/g, or 0.9 mmol/g. In this context, it may be noted that, during SPPS, the swelling and shrinking of the resin in the various solvents used can lead to considerable fluctuations of resin volume and hence peptide concentration on the resin.

In a preferred embodiment of the invention, the glucagon-like peptide is prepared by Fmoc-SPPS. Suitable protected amino acid derivatives (i.e., amino acid moieties conjugated to one or more protecting group(s)), such as Fmoc-Ala-OH, Fmoc-Arg(Pbf)-OH, Fmoc-Arg(Pmc)-OH, Fmoc-Asn(Trt)-OH, Fmoc-Asn(Mtt)-OH, Fmoc-Asp(OtBu)-OH, Fmoc-Asp (OMpe)-OH, Fmoc-Cys(Trt)-OH, Fmoc-Cys(Mmt)-OH, Fmoc-Gly-OH, Fmoc-Gln(Mtt)-OH, Fmoc-Gln(Trt)-OH, Fmoc-Glu(OtBu)-OH, Fmoc-His(1-Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, and Fmoc-Val-OH, are commercially available from various sources. It should be noted that the use of non-natural amino acid derivatives such as Aib (α-aminoisobutyric acid), Nle (norleucine), or Orn (ornithine) in the synthesis of glucagon-like peptides is likewise encompassed by the methods of the present invention. In a preferred embodiment, the amino acid derivatives Fmoc-Ala-OH, Fmoc-Arg(Pbf)-OH, Fmoc-Asp(OtBu)-OH, Fmoc-Asp(OMpe)-OH, Fmoc-Gly-OH, Fmoc-Gln(Trt)-OH, Fmoc-Glu(OtBu)-OH, Boc-His(Boc)-OH, Fmoc-His(1-Trt)-OH Fmoc-Ile-OH, Fmoc-Leu-OH, Fmoc-Phe-OH, Fmoc-Ser(tBu)-OH, Fmoc-Thr(tBu)-OH, Fmoc-Trp(Boc)-OH, Fmoc-Tyr(tBu)-OH, and Fmoc-Val-OH are used. The use of Fmoc-Trp(Boc)-OH with Fmoc-Arg(Pbf)-OH allows to suppress sulfonyl modification of tryptophan moieties by cationic species during peptide cleavage from the resin. However, as TFA cleavage from the resin may result in formation of side products such as carbamates, it can be advantageous to subject the crude peptide to a decarboxylation reaction. This may, exemplarily, be achieved by subjecting the crude peptide to a high pH treatment such as, e.g., a pH of at least 7.2, at least 8.0, at least 8.5, at least 9, at least 9.5, at least 10, at least 10.5, at least 11, or at least 11.5. Alternatively or additionally, decarboxylation reactions may be performed in mildly acid conditions such as, e.g. a pH of 6.0 to 7.0, pH of 5.5. to 6.5, or a pH of 5.0 to 6.0. Optionally, said treatments may be accompanied by a heat treatment, e.g., at a temperature of 30-70° C., for example at 30° C., 35° C., 40° C., 45° C., 50° C., 55° C., 60° C., 65° C., or 70° C.

The person skilled in the art is well-aware of SPPS methods based on an Fmoc synthesis protocol. Each cycle of amino acid addition to the resin typically starts with Fmoc cleavage, i.e., removal of the Fmoc protecting group from the resin-bound peptide chain. This is achieved by incubating the peptide resin with a base in a solvent capable of swelling the resin and dissolving the reagents. Popular bases for this purpose comprise, e.g., secondary amines such as piperidine and 4-methyl piperidine. Suitable solvents comprise, e.g., DMF, NMP, dimethyl sulfoxide, dichlormethane, tetrahydrofuran, acetonitrile, toluol, and mixtures thereof. The reaction is commonly carried out at ambient temperature, e.g. within a temperature range of 15-30° C. Usually, the base-labile and acid-stable Fmoc is split off by a short treatment (2 to 15 minutes, e.g. 2, 3, 4, 5, 6, 7, 8, 9, 10, 11, 12, 13, 14, or 15 minutes) with 5-50%, preferably 20%, piperidine in DMF (v/v).

Where necessary, this treatment is repeated and/or slightly prolonged (7 to 30 minutes, e.g. 7, 8, 9, 10, 11, 12, 13, 14, 15, 16, 17, 18, 19, 20, 21, 22, 23, 24, 25, 26, 27, 28, 29, or 30 minutes). For synthesis of large peptides with difficult-to-cleave stretches, the duration of Fmoc cleavage as well as the number of repetitions may be gradually increased. For instance, the cleavage time may be 15-75 minutes, e.g. 15, 30, 45, 60, or 75 minutes, and the cleavage may be repeated up to 8 times, e.g. 2, 3, 4, 5, 6, 7, or 8 times. Moreover, the temperature may be increased, e.g. to a temperature between 30° C. and 45° C. Under those conditions, complete deblocking is achieved in most cases. Additionally or alternatively, the reagent used for Fmoc cleavage may be varied.

It has been found that even slight variations of the reagent may considerably accelerate the cleavage, e.g. the use of: 1 to 5% DBU in DMF, 20% piperidine and 1-5% DBU in DMF, 20% piperidine in NMP, or 20% piperidine in DMF at 45° C. Moreover, acceleration of the cleavage reaction may be achieved by microwave treatment. On the other side, the nature of the peptide may render the use of milder treatments advantageous. Particular mild cleavage conditions are, e.g., 0.1 M HOBt plus 20% piperidine in DMF, 50% morpholine in DMF, 2% HOBt plus 2% hexamethyleneimine plus 25% N-methylpyrrolidine in 50% DMSO in NMP. The skilled person will routinely optimize and control Fmoc cleavage conditions at each step of the synthesis.

In a preferred embodiment, the Fmoc protecting group is cleaved off the growing peptide chain conjugated to the solid phase using a mixture selected from the group consisting of 5-50% (v/v) piperidine or 4-methyl piperidine in N,N-dimethylformamide (DMF), 5-50% (v/v) piperidine or 4-methyl piperidine in N-methylpyrrolidone (NMP), 1-5% (v/v) diazabicyclo[5.4.0]undec-7-ene (DBU) in DMF, and 50% (v/v) morpholine in DMF.

The cleavage reagent is typically washed out carefully after Fmoc-removal. DMF and optionally IPA are used for washing until neutral pH. To ensure complete base removal, it may be advantageous to add small amounts of HOBt in in later washing cycles.

The coupling of an amino acid derivative to the peptide resin, i.e. the elongation step, is one of the central steps of the SPPS cycle.

Rate and yield of the reaction may be influenced by various parameters such as the choice of solvent, the steric hindrance, and the reactivity of the activated carboxylic acid. The solvent may not only determine the swelling of the precursor peptide-resin and may thus influence the accessibility of the reactive sites; it may also directly affect the kinetics of the coupling reaction. Suitable solvents are capable of swelling the resin and dissolving the reagents and comprise, e.g., DMF, NMP, dimethyl sulfoxide, dichlormethane, tetrahydrofuran, acetonitrile, toluol, and mixtures thereof. The steric hindrance is determined by the nature of the amino acid side chains and their protecting groups. The reactivity of the activated carboxylic acid determines the acylation rate, as well as the extent of side reactions, such as racemization. Depending on the synthesis strategy chosen, peptide derivatives such as pseudoproline dipeptide derivatives, di-or tripeptide derivatives, or branched dipeptide derivatives may be used in lieu of single amino acid derivatives.

In certain embodiments of the present invention, amino acid activation is carried out in DMF as a solvent, i.e. the amino acid or peptide derivative, a coupling reagent and optionally an additive are dissolved in DMF and mixed. DIC may be used as coupling reagent in combination with either OXYMAPURE® (cyano-hydroxyimino-acetic acid ethyl ester), or HOBt as an additive. In the alternative, TBTU or DEPBT may be used to convert the Fmoc amino acid into an active OBt or ODhbt ester in the presence of a base, preferably DIPEA. The amino acid derivative of choice is pre-activated by incubation with the above reagents for 1-30 min, e.g. for 2, 3, 4, 5, 6, 7, 8, 9, 10, . . . , 28, 29, or 30 min before addition to the resin. The coupling reaction is allowed to proceed for 1 to 74 h, e.g. for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, . . . , 71, 72, 73, or 74 h. The amino acid derivative may be used in a 0.4-3 molar ratio relative to the amount of resin-bound amine groups, e.g. at a molar ratio of 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0. In order to achieve complete coupling, it may be advantageous to add a second portion of activating agent or base to the reaction mixture after some time, e.g. after 10, 20, 30, 40, or 60 min. The pre-activation and coupling steps are commonly carried out at room temperature, but may also be performed at other temperatures. It may be advantageous to perform one or more re-coupling steps in order to achieve near to complete conversion of amino groups.

In other embodiments of the invention, amino acid activation is carried out in a solvent consisting of NMP, dimethyl sulfoxide, dichlormethane, tetrahydrofuran, acetonitrile, toluol, and mixtures thereof, optionally with DMF.

In a preferred embodiment, step (i-a) of the present invention comprises Fmoc-based Solid Phase Peptide Synthesis (SPPS) using suitably protected amino acid derivatives or dipeptide derivatives, wherein said protected amino acid derivatives or dipeptide derivatives are activated by means of one or more coupling reagent/additive mixtures selected for each step independently from the group consisting of (A) TBTU/DIPEA;
(B) DIC/OXYMAPURE® (cyano-hydroxyimino-acetic acid ethyl ester);
(C) DEPBT/DIPEA; and
(D) DIC/HOBt.

The coupling of His derivatives is preferably carried out so as to avoid racemization. This side reaction can be reduced by three different approaches: 1) blocking of the N3 of the imidazole ring, 2) blocking of the N1 of the imidazole ring by electron withdrawing groups such as Boc or Tos, and 3) optimization of coupling conditions when using Fmoc-His(1-Trit)-OH. It is therefore recommended to use Fmoc-His(1-Trit)-OH, Boc-His(1-Trt)-OH, or Boc-His(Boc)-OH, most preferably Boc-His(Boc)-OH, in combination with DEPBT/DIPEA to introduce an N-terminal His.

Therefore, in a preferred embodiment, the N-terminal histidine moiety is introduced into the precursor peptide conjugated to the solid phase using an amino acid derivative selected from the group consisting of Boc-His(Boc)-OH, Boc-His(1-Trt)-OH, and Fmoc-His(1-Trt)-OH and the coupling reagent/additive mixture DEPBT/DIPEA.

Capping may be performed to block unreacted amines from peptide bond formation in the following steps of synthesis, i.e., to avoid the formation of deletion variants of the sequence to be synthesized. This may be achieved by a short treatment of the peptide resin with a large excess of a highly reactive unhindered acid derivative, e.g. N-hydroxysuccinimide, acetic anhydride or benzoyl chloride, and a base, e.g. pyridine, collidine, or DIPEA, optionally in the presence of an additive such as OXYMAPURE® (cyanohydroxyimino-acetic acid ethyl ester), or HOBt. Capping will typically yield a truncated sequence, which generally differs considerably from the final peptide and can be readily separated. Preferably, systematic double coupling is followed by capping. At the end of the capping step, the reagents are typically filtered off and the resin is carefully washed, e.g. with DMF and optionally IPA, before proceeding to the next deprotection step.

Preferably, on-resin aggregation of the glucagon-like peptide, e.g. of Liraglutide, is prevented during SPPS.

Glucagon-like peptides such as Liraglutide intrinsically tend to aggregate, which represents an additional challenge for their efficient synthesis. Stepwise Fmoc-SPPS may become comparably difficult or even fail as soon as the resin-bound peptide aggregates.

There are many possible options to mitigate such aggregation, including control of resin load by control of coupling density, control of resin shrinking during washing steps, addition of solvents such as DMSO, addition of chaotropic salts, addition of nonionic detergents and of ethylene carbonate, performing the coupling reaction at elevated temperature/under microwave treatment, and sonication of the coupling reaction mixture.

Further possible measures include introduction of at least one O-isoacyl peptide bond to serine or threonine, introduction of at least one pseudo proline dipeptide, or N-alkylation of at least one peptide bond by 2-hydroxy-4-methoxybenzyl (Hmb) or 2,4-dimethoxybenzyl (Dmb) moieties. Accordingly, at least one dipeptide derivative comprising a O-isoacyl peptide bond such as Boc-Ser(Val-Fmoc)-OH or Boc-Thr(Gly-Fmoc)-OH may be used for this purpose. Alternatively or additionally, at least one dipeptide with an N-alkylated peptide bond such as Fmoc-Glu(OtBu)-(Dmb)Gly-OH and Fmoc-Ala-(Dmb)Ala-OH may be used.

It has surprisingly been found that the use of at least one Fmoc pseudoproline dipeptide advantageously suppresses peptide aggregation and hence the formation of by-products due to inefficient synthesis. Preferably, the pseudoproline dipeptide is introduced at a position corresponding to or identical with a position selected from $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of formula I.

Thus, the introduction of a pseudoproline moiety results in the provision of a solid-phase conjugated glucagon like peptide, preferably a solid-phase conjugated Liraglutide, which is characterized by a reduced percentage of related impurities. A variety of pseudoproline dipeptide derivatives are known by the person skilled in the art (cf., brochure "Pseudoproline Dipeptides Bachem—Pioneering Partner for Peptides", published by Global Marketing, Bachem Group, November 2015). Therefore, in a preferred embodiment, one or more pseudoproline dipeptides are introduced at a position selected from the group consisting of $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of formula I.

In a particularly preferred embodiment, one or more pseudoproline dipeptide derivatives selected from the group consisting of Fmoc-Gly-Thr(Psi(Me,Me)pro)-OH, Fmoc-Phe-Thr(Psi(Me,Me)pro)-OH, Fmoc-Thr(tBu)-Ser(Psi(Me,Me)pro)-OH, Fmoc-Val-Ser(Psi(Me,Me)pro)-OH, and Fmoc-Ser(tBu)-Ser(Psi(Me,Me)pro)-OH is/are used.

According to a preferred embodiment, one or more pseudoproline dipeptide/s is/are introduced at a position identical with or corresponding to a position selected from the group consisting of $Gly^4$-$Thr^5$, $Phe^6$-$Thr^7$, or $Thr^7$-$Ser^8$ of the peptide of formula I. Preferably, a single pseudoproline dipeptide is introduced at a position corresponding to or identical with $Thr^7$-$Ser^8$ of the peptide of formula I. In another preferred embodiment, a single pseudoproline dipeptide is introduced at a position corresponding to or identical with $Phe^6$-$Thr^7$ of the peptide of formula I. In a particularly preferred embodiment, one or more pseudoproline dipeptide/s selected from the group consisting of Fmoc-Gly-Thr(Psi(Me,Me)pro)-OH, Fmoc-Phe-Thr(Psi(Me,Me)pro)-OH, or Fmoc-Thr(tBu)-Ser(Psi(Me,Me)pro)-OH are used.

According to a preferred embodiment, the only pseudoproline dipeptide/s introduced is/are located at positions identical with or corresponding to a position selected from the group consisting of $Gly^4$-$Thr^5$, $Phe^6$-$Thr^7$, or $Thr^7$-$Ser^8$ of the peptide of formula I. In a particularly preferred embodiment, the only pseudoproline dipeptide/s introduced is/are selected from the group consisting of Fmoc-Gly-Thr(Psi(Me,Me)pro)-OH, Fmoc-Phe-Thr(Psi(Me,Me)pro)-OH, or Fmoc-Thr(tBu)-Ser(Psi(Me,Me)pro)-OH.

According to a preferred embodiment, a single pseudoproline dipeptide is introduced at a position identical with or corresponding to a position selected from the group consisting of $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of formula I, preferably selected from the group consisting of $Gly^4$-$Thr^5$, $Phe^6$-$Thr^7$, and $Thr^7$-$Ser^8$ of the peptide of formula I. In a particularly preferred embodiment, a single pseudoproline dipeptide selected from the group consisting of Fmoc-Gly-Thr(Psi(Me,Me)pro)-OH, Fmoc-Phe-Thr(Psi(Me,Me)pro)-OH, or Fmoc-Thr(tBu)-Ser(Psi(Me,Me)pro)-OH is used.

The term "pseudoproline dipeptides" as used herein refers to temporary proline mimics, which can be readily obtained from Ser and Thr by oxazolidine formation and from Cys by thiazolidine formation. The person skilled in the art is well-aware of such pseudoproline dipeptides. These dipeptides are one possible option to mititgate on-resin aggregation during SPPS. The 2,2-dimethyloxazolidines are smoothly cleaved by TFA and thus particularly suitable for Fmoc-SPPS. Hence, in particular Fmoc-Phe-Thr(Psi(Me,Me)pro)-OH, or Fmoc-Gly-Thr(Psi(Me,Me)pro)-OH, Fmoc-Thr(tBu)-Ser(Psi(Me,Me)pro)-OH, Fmoc-Val-Ser(Psi(Me,Me)pro)-OH, and Fmoc-Ser(tBu)-Ser(Psi(Me,Me)pro)-OH may be used.

The term "a position corresponding to a position selected from $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of formula I" as used herein refers to a position within the primary sequence of a glucagon-like peptide, which position is considered homologous to a position selected from $Gly^4$-$Thr^5$, $Phe^6$-$Thr^7$, $Thr^7$-$Ser^8$, $Val^{10}$-$Ser^{11}$ or $Ser^{11}$-$Ser^{12}$ of the peptide of formula I, based on a sequence alignment of said glucagon-like peptide with the peptide of formula I. Typically, the positions which are displayed on top of each other in such an alignment are considered to be homologous, i.e. to correspond to each other. Typical sequence alignment tools such as BLAST or ClustalW are well known to the person skilled in the art.

As laid out above, Liraglutide may comprise a palmitic acid conjugated to a glutamyl residue bound to the epsilon amino group of lysyl moiety at amino acid position 20 (Lys[20]), i.e., Lys(palmitoyl-Glu-OH). This may be introduced by any means.

Various protocols can be used for the introduction of a (Nε-(γ-glutamyl(Nα fatty acid ester))) substituted Lys side chain (cf., e.g., U.S. Pat. No. 6,451,974, EP-A 2 757 107, WO 2013/171135). In the context of the present invention, it is preferred to introduce said group at least in part during SPPS by using a branched dipeptide building block of the below formula 2, wherein $R_3$ is an amino protecting group, $R_1$ is an carboxylic acid protecting group, and $R_2$ is either an amino protecting group or fatty acid moiety, in particular a palmitoyl [$CH_3(CH_2)_{14}CO$—] group.

Formula 2

Particularly preferably, SPPS is performed by using either an Fmoc-Lys(palmitoyl-Glu-OtBu)-OH building block (commercially available, e.g., from Iris Biotech GmbH or from Peptides International) or an Fmoc-Lys(Boc-Glu-OtBu)-OH building block (commercially available, e.g., from Active Peptide).

In case the latter is used, the resulting peptide may be N-palmitoylated at the alpha amino function of the glutamyl moiety. Various activated esters of palmitic acid, e.g. p-nitrophenyl and succinimide esters can be used for this purpose. In a preferred embodiment, N-succinimidyl palmitate is used.

Therefore, in a preferred embodiment, the method comprises a step of reacting the peptide with an activated ester of palmitic acid, preferably with N-succinimidyl palmitate. This will typically lead to the peptide of formula I.

In a more preferred embodiment, the method comprises a step of reacting an activated ester of palmitic acid, preferably N-succinimidyl palmitate, with the Lys(H-Glu-OH) moiety of the peptide of formula I or with a Lys(H-Glu-$OR_1$) moiety obtainable by cleaving off the amino protecting group $R_2$ from the precursor peptide provided in step (i-a).

Even more preferably, the method comprises a step of reacting an activated ester of palmitic acid, preferably N-succinimidyl palmitate, with a Lys(H-Glu-$OR_1$) moiety obtainable by cleaving off the amino protecting group $R_2$ from the precursor peptide provided in step (i-a), in particular wherein the precursor peptide provided in step (i-a) bears at least protecting groups at the side chains of Glu, Asp and Lys.

Optionally, the progress of the SPPS reaction may be monitored using in process controls to ensure efficient Fmoc removal, coupling, and/or capping steps. Fmoc determination on one hand and determination of free amines on the other hand may result in complementary information. Taken together, these methods may enable efficient monitoring of each step of the SPPS process. Some of the common monitoring methods usable in the context of the present invention are exemplified below.

Optionally, the amount of Fmoc cleaved from the resin-bound peptide may easily be quantified, e.g., by spectrometric determination. The Fmoc cleavage reagent drained from the resin may be collected and the Fmoc concentration therein determined, e.g. by measuring the absorbance at 301 nm. Based on the amount of Fmoc cleaved off, the resin load, i.e. the original amount of Fmoc peptide on the resin, may be calculated. Further, to assess the completeness of Fmoc removal, a small sample of presumably Fmoc-deprotected resin may be subjected to an additional harsh Fmoc cleavage protocol in order to determine the amount of residual Fmoc removed by this treatment. In the alternative, a small scale test cleavage of the peptide from a resin sample may be carried out in order to assess the completeness of Fmoc removal. The resulting peptides may be analyzed by analytical RP-HPLC using a standard gradient, where Fmoc protected and free peptide sequences are usually well separated. Additionally or alternatively, the peptide sample may be analyzed by mass spectrometry, e.g. by LC-MS or MALDI-MS. Thin layer chromatography likewise may enable the detection of minute amounts of Fmoc peptides.

The amount of free amines on the resin may be assessed by various assays, including the colorimetric Kaiser (i.e. Ninhydrin), TNBS, Chloranil, and Bromophenol Blue tests. This is well-known to a person skilled in the art.

These tests may advantageously be used to assess the generation of free amino functions after Fmoc-cleavage, as well as their disappearance after coupling of the following Fmoc-protected amino acid derivative and/or after a capping step. Preferably, at least two colorimetric tests such as the Kaiser and the TNBS tests may be carried out in parallel. The Kaiser test is based on the reaction of ninhydrin with amines. It is a very sensitive test for primary amines, visualized by an intense blue color, and somewhat less suitable for secondary amines, which yield a brownish red color. The color usually develops mainly in the beads and partly in the supernatant. When a spectrometric quantitation of the amount of unreacted amino groups is intended, the color may be transferred completely to the solution. The intensity of the color depends on the nature of the amino terminus to be detected. Rather unspecific shades are obtained with N-terminal, sidechain protected Asp, Asn, Cys, Ser, and Thr and brownish red beads result with N-terminal Pro. As the resin sample is typically heated, "hidden" $NH_2$-groups may become more accessible and thus detectable.

However, prolonged heating as well as overheating should be avoided as it may cause cleavage of Lys(Boc) or Fmoc removal (by pyridine). The TNBS (2,4,6-trinitrobenzenesulfonicacid) test is nearly as sensitive as the Kaiser test, but can only be used for detecting primary amino groups. Only the beads will turn orange-red and the intensity of the color does not depend on the nature of the N-terminal amino acid. As a slightly orange staining in the core of the beads cannot be detected by simple visual inspection, it is recommended to use more sensitive read-outs, e.g. to inspect the beads under a microscope.

When the synthesis of the precursor peptide by SPPS is completed, it is still conjugated to the resin. Thus, it is solid phase bound and at least partly side-chain protected. To obtain the peptide of formula I, e.g. Liraglutide or any other glucacon-like peptide of the present invention, the peptide is cleaved off the resin. This is herein represented by step (i-b) of cleaving the precursor peptide off the resin.

Most preferably, during this step, also most or all of the side chain protecting groups are concomitantly cleaved off the peptide, i.e., the peptide is deprotected, thereby providing the peptide of formula I.

Therefore, preferably, deprotection and cleavage from the resin (step (i-b)) are carried out concomitantly by incubation with a cleavage composition comprising TFA and one or more scavengers.

For cleaving the peptide off the resin, any composition suitable for this purpose may be used. Preferably, cleavage and deprotection is conducted by means of a composition comprising more than 50% (v/v) TFA, more preferably more than 75% (v/v) TFA, in particular at least 80% (v/v) or even at least 90% (v/v) TFA. The composition may also comprise water and/or one or more scavengers. Preferably, the composition comprises TFA, water and one or more scavengers. Particularly advantageous scavengers are thiol scavengers such as EDT and/or silane scavengers such as, e.g., TIPS. The cleavage composition may comprise at least 80% TFA, preferably at least 90% TFA, and EDT. The cleavage composition may comprise at least 80% TFA, preferably at least 90% TFA, water, and EDT. The cleavage composition may comprise at least 80% TFA, preferably at least 90% TFA, water, and TIPS. The cleavage composition may comprise at least 80% TFA, preferably at least 90% TFA, water, TIPS and EDT. Exemplary, compositions for use in the context of the present invention may be selected from the group consisting of TFA/water/TIPS (90:5:5) v/v/v, TFA/water/phenol (90:5:5) v/v/v, TFA/water/EDT/TIPS (90:5:2.5:2.5) v/v/v/v, TFA/water/EDT/TIPS (90:4:3:3) v/v/v/v, TFA/water/EDT (90:5:5) v/v/v, TFA/thioanisole/anisole/EDT (90:5:3:2) v/v/v/v and TFA/thioanisole/water/phenol/EDT (82.5:5:5:5:2.5) v/v/v/v/v.

The step of cleaving the precursor peptide off the resin (step (i-b)) may be carried out at any conditions suitable for this purpose. Cleavage is preferably carried out (preferably under inert gas) by incubating the washed resin with the cleavage composition for about 1 to 4 h and/or at a temperature of 0 to 32° C.

Exemplarily, cleavage may be carried out (preferably under inert gas) by incubating the washed resin with the cleavage composition for up to 1, up to 1.5, up to 2, up to 2.5, up to 3, up to 3.5 or up to 4 h or longer than 4 h at a temperature of about 0 to 4° C., 4 to 10° C., 10-15° C., 15 to 25° C., or 25 to 35° C. Exemplarily, cleavage may be carried out (preferably under inert gas) by incubating the washed resin with the cleavage composition for up to 1, up to 1.5, up to 2, up to 2.5, up to 3, up to 3.5 or up to 4 h or longer than 4 h at a temperature of about 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, or 32° C.

Alternatively, another cleavage composition may be used. For example, the cleavage of protected peptide fragments from 2-Chlorotrityl resin may be achieved using TFE/AcOH/DCM (1:1:3), 0.5% TFA/DCM, or HFIP/DCM.

The person skilled in the art will routinely optimize the compositions for use in the context of the present invention depending on the amino acid composition of the peptide in question and will envisage the optional use of one or more scavengers such as, inter alia, DTE, EDT, TES, TIPS, 2-mercaptoethanol, ethyl methyl sulfide, m- or p-cresol, 2-Me-indole, Ac-Trp-OMe, or tryptamine.

In the context of the present application, the term "scavengers" is used to refer to compounds which are added to the reaction mixture in order to suppress side reactions during cleavage of a peptide from the resin after SPPS and/or during removal of protecting groups. Typical scavengers used in a cleavage composition are "thiol scavengers" (e.g. EDT, DTE, DTT, and beta-mercaptoethanol) and "silane scavengers" (e.g. TES and TIPS). Further commonly used scavengers comprise ethyl methyl sulfide, thioanisole, anisole, m- or p-cresol, 2-Me-indole, Ac-Trp-OMe, or tryptamine. The person skilled in the art is well-aware of a large variety of scavengers usable.

According to the above, the solution S obtained from step (i) preferably also comprises TFA (typically at least 80% (v/v) or at least 90% (v/v)), the residuals of protecting groups cleaved off the peptide and, more preferably, also water, and one or more scavengers.

The resin is then separated, usually by filtration, from the solution S obtained from step (i), i.e., by cleaving the peptide off the resin. In an embodiment of the invention, said solution S obtained from step (i) comprises the Liraglutide peptide and the regents used for cleavage (e.g., TFA, water, scavengers, and residuals of the protecting groups cleaved off the peptide). Optionally, the resin is rinsed after filtration, e.g. with concentrated TFA or with concentrated TFA plus scavengers. Optionally, the additional rinsing solutions may also form part of the solution S obtained from step (i), i.e., they may be pooled with the solution obtained directly after cleavage of the peptide from the resin.

Therefore, in a preferred embodiment, the solution S obtained from step (i) further comprises trifluoroacetic acid (TFA), water and one or more scavengers.

In a more preferred embodiment, the solution S obtained from step (i) comprises trifluoroacetic acid (TFA), water and one or more scavengers selected from thiol scavengers and/or silane scavengers.

The scavengers may serve to prevent undesired side reactions with sensitive amino acids such as Cys, Met, Ser, Thr, Trp, and Tyr. Without wishing to be bound by any theory, it is believed that said side reactions are suppressed by capture of the highly reactive carbocations generated during the cleavage reaction.

The person skilled in the art will note that it is desirable to isolate the peptide of formula I from the solution S, thereby obtaining a crude peptide (typically present as the TFA salt). In a particularly preferred embodiment of the present invention, this is performed by precipitation of the peptide of step (i) by means of an anti-solvent comprising diisopropyl ether (IPE) and acetonitrile (ACN), wherein the volume ratio (IPE:ACN) is in the range of from (3:1) to (10:1); and subsequently isolating the obtained precipitate.

Herein, the mixture of IPE and ACN serves as an anti-solvent. This term is well understood by a person skilled in the art. As used herein, the term "anti-solvent" may be understood in the broadest sense as any reagent which induces peptide precipitation when mixed with a peptide solution. Exemplary, anti-solvents may comprise diethyl ether, IPE, MTBE, and mixtures of IPE with ACN. According to the present invention, the anti-solvent comprises IPE and ACN in a ratio selected from the range of (3:1) v/v to (10:1) v/v. More preferably, the anti-solvent comprises IPE and ACN, wherein the volume ratio (IPE:ACN) is in the range of from (3:1) to (5:1). Surprisingly, it has been found that recovery of the crude peptide from the cleavage composition is particularly good when employing an anti-solvent comprising IPE and ACN in a ratio selected from the range of (3:1) v/v to (10:1) v/v, preferably in a ratio of (3:1) to (5:1) v/v, e.g. in a ratio of (3:1), (3.5:1), (4:1), (4.5:1), or (5:1) v/v.

The use of said anti-solvent was found to improve purity and physical properties of the precipitate, thereby enabling efficient separation of the peptide product from the cleavage composition.

Advantageously, the present invention allows fast recovery of the crude peptide by enabling the formation of non-sticky precipitates whose size distribution enables fast filtration. Further advantageous is the precipitate's purity and a low TFA content.

In a preferred embodiment, the anti-solvent used in step (ii) comprises at least 50% (v/v) of a mixture M consisting of diisopropyl ether and acetonitrile, preferably the anti-solvent comprises at least 75% (v/v) of said mixture M, more preferably the anti-solvent essentially consists of a mixture of diisopropyl ether and acetonitrile.

In a particularly preferred embodiment, the anti-solvent essentially consists of a mixture of diisopropyl ether and acetonitrile wherein the volume ratio (diisopropyl ether: acetonitrile) is in the range of from (3:1) to (5:1).

The anti-solvent may be mixed with solution S by any means. In a preferred embodiment, step (ii) comprises mixing the anti-solvent with solution S obtained from step (i) by means of:
(ii-a) pre-mixing diisopropyl ether and acetonitrile before mixing it with the solution S obtained from step (i);
(ii-b) first mixing diisopropyl ether with the solution S obtained from step (i) and subsequently mixing acetonitrile with the mixture comprising solution S and diisopropyl ether; or
(ii-c) first mixing acetonitrile with the solution S obtained from step (i) and subsequently mixing diisopropyl ether with the mixture comprising solution S and acetonitrile.

In other words, the anti-solvent may be divided in an acetonitrile containing part and a diisopropyl ether containing part and said parts are contacted subsequently with the solution comprising the peptide. Alternatively, the anti-solvent is a single liquid mixture.

In sum, the (IPE:ACN) volume range of the present invention is finally obtained. The person skilled in the art will understand that aliquots of acetonitrile and diisopropyl ether may also be alternately mixed with the solution S to sum up at a volume range of the present invention.

Preferably, the volume ratio of solution S to antisolvent is in the range of 1:5 to 1:15, e.g. 1:5, 1:8, 1:10, 1:12, or 1:15. In other words: one volume of solution S may be mixed with an amount of antisolvent corresponding to, e.g., 5, 6, 7, 8, 9, 10, 11, 12, 13, 14, or 15 volumes.

The step of precipitation of the peptide of formula I out of the solution S (step (ii)) may be conducted at any temperature and any time interval suitable for this purpose. Exemplarily, step (ii) is carried out at −5° C. to 25° C., e.g. about −5-0° C., 0-10° C., 10-20° C., or 20-25° C.

As used in the context of the present application, the term "about" is used to indicate deviations of up to 10% from any given numerical value.

In a preferred embodiment, precipitation of the peptide of formula I (step (ii)) is carried out at a temperature in the range of −5° C. to 10° C., preferably 0° C. to 10° C. Suitable temperature ranges may be −5-0° C., −2.5-2.5° C., 0-5° C., 2.5-7.5° C., or 5-10° C.

Exemplarily, step (ii) is carried out for a time interval of about 30 to 360 min, e.g. about 30, 60, 90, 120, 150, 180, 210, 240, 270, 300, 330, or 360 min.

Preferable precipitation conditions are thus characterized by a temperature in the range of about −5° C. to 25° C., e.g. about −5-0° C., 0-10° C., 10-20° C., or 20-25° C. and by a reaction time in the range of around 30 to 360 minutes, e.g. about 30, 60, 90, 120, 150, 180, 210, 240, 270, 300, 330, or 360 minutes.

In a particularly preferred embodiment, the method for preparing a Liraglutide peptide or a salt thereof, comprises:
(i) providing a solution S comprising a peptide of formula I:

His-Ala-Glu-Gly-Thr-Phe-Thr-Ser-Asp-Val-Ser-Ser-Tyr-Leu-Glu-Gly-Gln-Ala-Ala-$B^1$-Glu Phe-Ile-Ala-Trp-Leu-Val-Arg-Gly-Arg-Gly, wherein $B^1$ is Lys(palmitoyl-Glu-OH) or Lys(H-Glu-OH);
wherein the provision of said solution S comprises:
(i-a) providing a precursor peptide conjugated to a solid phase:
H-His-Ala-Glu-Gly-Thr-Phe-Thr-Ser-Asp-Val-Ser-Ser-Tyr-Leu-Glu-Gly-Gln-Ala-Ala-$B^2$-Glu-Phe-Ile-Ala-Trp-Leu-Val-Arg-Gly-Arg-Gly-[resin],
wherein $B^2$ is Lys(palmitoyl-Glu-OtBu) or Lys(Boc-Glu-OtBu) and
wherein at least the side chains of Glu, Asp, and Lys bear protecting groups; and
(i-b) cleaving the precursor peptide off the resin by means of an cleavage composition comprising trifluoroacetic acid (TFA),
wherein said solution S obtained from step (i) comprises trifluoroacetic acid (TFA), water and one or more scavengers selected from thiol scavengers and/or silane scavengers;
(ii) precipitation of the peptide of step (i) by means of mixing solution S with an anti-solvent consisting of diisopropyl ether and acetonitrile, wherein the volume ratio (diisopropyl ether:acetonitrile) is in the range of from (3:1) to (5:1); and
(iii) isolating the precipitate obtained from step (ii), preferably by means of filtration and/or centrifugation.

The solution S obtained from step (i) and the anti-solvent may be mixed by any means known in the art. The solution S obtained from step (i) and the anti-solvent may be mixed in any order.

According to a preferred embodiment, step (ii) is carried out using a classical precipitation protocol, i.e. the anti-solvent is added to the solution S obtained from step (i). This may be achieved by adding it at once or by adding it dropwise and/or by means of a slow flow.

According to another preferred embodiment, step (ii) is carried out using an inverse precipitation protocol, i.e. the solution S obtained from step (i) is added to the anti-solvent. This may be achieved by adding it at once or by adding it dropwise and/or by means of a slow flow. The person skilled in the art is well-aware of how to conduct such precipitation steps.

The precipitate comprising the Liraglutide peptide is then formed as a suspension in the anti-solvent, wherein said suspension further comprises the reagents of the cleavage composition (e.g., TFA, water, and scavengers) as well as the residuals of the protecting groups cleaved off the peptide. The precipitate comprising (or essentially consisting of) the Liraglutide peptide may then be isolated from the crude suspension by any means known for such purpose in the art.

The present invention hence also comprises the step (iii) of isolating the precipitate obtained from step (ii).

According to a preferred embodiment, this step (iii) is accomplished by means of filtration and/or centrifugation.

As used herein the term "isolating" may be understood in the broadest sense as any means for obtaining a product of interest, e.g. a crude peptide precipitate, from a more complex composition. A crude peptide precipitate may comprise at least 30% (w/w), preferably at least 40% (w/w), more preferably at least 50% (w/w), more preferably at least 60% (w/w), more preferably at least 70% (w/w), even more preferably at least 80% (w/w), even more preferably at least 90% (w/w), in particular at least 95% (w/w) or even 100% (w/w) of the Liraglutide peptide in the dry state. Typically, a crude peptide precipitate comprises 40-70% (w/w) of the Liraglutide peptide in the dry state.

Filtration may be any filtration method known in the art, such as, e.g., dead-end filtration or cross-flow filtration. As used herein, the terms "cross-flow filtration", "crossflow filtration", "tangential flow filtration" or "tangential filtration" may be understood interchangeably. The filter may be of any material known in the context of filtration in the art, such as, e.g., plastic (e.g., nylon, polystyrene), metal, alloy, glass, ceramics, cellophane, cellulose, or composite material. The filter may be hydrophobic or hydrophilic. The surface of the filter may be neutral or positively charged or negatively charged.

Centrifugation may be understood in the broadest sense as any means wherein the sedimentation of the suspended precipitate is accelerated. Exemplarily, a centrifugal force of up to 100×g, at least 100×g, at least 1,000×g, at least 2,500×g, at least 5,000×g, at least 7,500×g, at least 10,000× g, at least 15,000×g, at least 25,000×g, or at least at least 50,000×g may be used. By means of centrifugation, a cake comprising (or (essentially) consisting of) the crude Liraglutide peptide is formed. Optionally, the cake may be resuspended in an anti-solvent which may be identical or different to the above-referenced anti-solvents. Optionally, centrifugation and resupending the pellet in an anti-solvent may be reiterated several times which may increase the purity of the crude Liraglutide peptide further.

Preferably, the crude peptide obtained by the method of the present invention can be subjected to further purification by one or more preparative process steps. Means for purification and separation, which may optionally be used in this context, comprise, e.g., one or more electrophoretic methods (e.g., gel electrophoresis or capillary (CE) electrophoresis), one or more additional precipitation-based methods (e.g., salting in or salting out), one or more dialytical methods (dialysis), and/or one or more chromatographic methods (e.g., gel permeation chromatography (GPC), size exclusion chromatography, Ion exchange chromatography (IEC), high performance liquid chromatography (HPLC), reversed phase HPLC (RP-HPLC), fast protein liquid chromatography (FPLC), Flash Chromatography (flash), Rapid Refluid Liquid Chromatography (RRLC), Rapid Separation Liquid Chromatography (RSLC), Ultra Fast Liquid Chromatography (UFLC), reversed phase UFLC (RP-UFLC), Ultra Performance Liquid Chromatography (UPLC) or reversed phase UPLC (RP-UPLC) Preferably, the crude peptide is first subjected to three-dimensional reversed phase HPLC followed by size exclusion chromatography, ion exchange chromatography, or ultrafiltration.

The person skilled in the art will notice that the present invention also embraces a crude Liraglutide peptide precipitate of improved purity which is particularly easy to handle due to improved particle size and consistency.

Therefore, a further aspect of the present invention refers to a Liraglutide peptide precipitate, obtainable or obtained by a method according to the present invention. In a preferred embodiment, the Liraglutide peptide precipitate obtainable from a method according to the present invention is characterized by a mean particle size of above 280 micrometers, above 300 micrometers, above 350 micrometers, or above 400 micrometers.

Moreover, the Liraglutide peptide precipitate obtainable from a method according to the present invention may be characterized by a peptide purity of at least 50%, preferably at least 55%, and more preferably at least 60%.

In preferred embodiments, the Liraglutide peptide precipitate obtainable from a method according to the present invention may be characterized by containing N-terminally and/or C-terminally truncated Liraglutide variants. In some embodiments, the Liraglutide peptide precipitate obtainable from a method according to the present invention may be characterized by containing the truncated variant Liraglutide 21-31-OH, which may be acylated, e.g. acetylated, at N-terminus. In other embodiments, the Liraglutide peptide precipitate obtainable from a method according to the present invention may be characterized by containing the truncated variant Liraglutide 1-30.

The term "truncated variant" as used herein refers to continuous fragments, i.e. subsequences without gaps, of said peptide, which lack one or more amino acids at the N-terminus or the C-terminus of the peptide sequence. N-terminally truncated variants may be acylated, e.g. acetylated.

In further preferred embodiments, the Liraglutide peptide precipitate obtainable by the present invention may be characterized by a decreased or even lack of stickiness and/or by a TFA content of below 20% (w/w). In a particularly preferred embodiment, the Liraglutide peptide precipitate obtainable by the present invention is characterized by a mean particle size of above 350 micrometers and a purity of at least 55%. In another preferred embodiment, the Liraglutide peptide precipitate obtainable by the present invention is characterized by a mean particle size of above 400 micrometers and a purity of at least 55%. In another preferred embodiment, the Liraglutide peptide precipitate obtainable by the present invention is characterized by a mean particle size of above 350 micrometers and a purity of at least 60%. In a particularly preferred embodiment, the Liraglutide peptide precipitate obtainable by the present invention is characterized by a mean particle size of above 350 micrometers, a purity of at least 55%, and a non-sticking consistency. In yet another preferred embodiment, the Liraglutide peptide precipitate obtainable by the present invention is characterized by a mean particle size of above 350 micrometers, a purity of at least 55%, and an TFA content below 20% (w/w).

The particle size of a precipitate may be measured by any means in the art, e.g. by Focused Beam Reflectance Measurement (FBRM) technology as described below.

Unless noted otherwise, peptide purity is indicated herein as "HPLC purity", i.e. as relative peak area observed in analytical reversed phase high performance liquid chromatography (RP-HPLC) with UV detection at a wavelength between 205 and 230 nm, i.e. at the absorption maximum of the peptide bond. In other words, the value is determined as % area of a given peak area divided by the sum of the areas of all observed peaks in a chromatogram obtained by analytical RP-HPLC with UV detection at a wavelength between 205 and 230 nm. This measure is common practice in the field, and the skilled person will routinely devise a product specific RP-HPLC protocol and perform the quantification according to the established guidelines set out in the United States Pharmacopeia. The suitability of the RP-HPLC protocol for the detection of peptidic contaminations is routinely assessed by determining the peak purity by LC-MS. Under the assumption that, due to their similar structure, all peptidic components have the same absorption, the RP-HPLC purity can be used as a proxy for a purity expressed as mass percentage [% (w/w)].

In the context of said Liraglutide peptide precipitate, all definitions laid out above also apply. The person skilled in the art will notice that the liraglutide peptide in said precipitate may be in form of a salt, in particular a TFA salt.

Optionally, one or more amino acid moieties of the Liraglutide peptide of the present invention may subsequent to obtaining the peptide be lipidated, phosphorylated, sulfated, cyclized, oxidized, reduced, decarboxylated, acetylated, acylated, amidated, deamidated, biotinylated or bound to one or more other small molecules and/or terpenes. Optionally, the Liraglutide peptide of the present invention may be labeled by one or more small molecule dyes (e.g., Cy dyes (e.g., Cy3, Cy5, Cy5.5, Cy7), Alexa dye/s (e.g., Alexa Fluor 488, Alexa Fluor 546, Alexa Fluor 647, Alexa Fluor 680, Alexa Fluor 750), VisEn dyes (e.g. VivoTag680, VivoTag750), S dyes (e.g., S0387), DyLight fluorophores (e.g., DyLight 750, DyLight 800), IRDyes (e.g., IRDye 680, IRDye 800), fluorescein dyes (e.g., fluorescein, carboxyfluorescein, fluorescein isothiocyanate (FITC)), rhodamine dyes (e.g., rhodamine, tetramethylrhodamine (TAMRA)) or HOECHST dyes) or one or more quantum dots.

As laid out above, according to preferred embodiments of the method according to the present invention, the Liraglutide peptide is prepared by SPPS on a resin.

Therefore, a still further aspect of the present invention relates to a precursor peptide conjugated to a resin:

```
His-Ala-Glu-Gly-Thr-Phe-Thr-Ser-Asp-Val-Ser-Ser-
Tyr-Leu-Glu-Gly-Gln-Ala-Ala-B²-Glu-Phe-Ile-Ala-
Trp-Leu-Val-Arg-Gly-Arg-Gly-[resin],
``` wherein $B^2$ is Lys (palmitoyl-Glu-OR$_1$) or $B^2$ is Lys (R$_2$-Glu-OR$_1$), with R$_1$ being a carboxylic acid protecting group and R$_2$ being an amino protecting group, wherein at least the side chains of Glu, Asp, and Lys bear protecting groups, and wherein at least one pseudoproline dipeptide is present at a position selected from the group consisting of Gly$^4$-Thr$^5$, Phe$^6$-Thr$^7$, Thr$^7$-Ser$^8$, Val$^{10}$-Ser$^{11}$ or Ser$^{11}$-Ser$^{12}$.

In the context of said precursor peptide, all definitions laid out above also apply. The person skilled in the art will notice that also salts, in particular pharmaceutical acceptable salts, of said precursor peptides are also embraced by the present invention. In a preferred embodiment, at least one pseudoproline is present at a position selected from Gly$^4$-Thr$^5$, Phe$^6$-Thr$^7$, or Thr$^7$-Ser$^8$ of the precursor peptide. This may exemplarily be a pseudoproline moiety as described herein.

As used herein, the term "precursor peptide" may be understood in the broadest sense as a compound that can be converted into a peptide in the sense of the present invention, i.e., a glucagon-like peptide, in particular Liraglutide. Typically, such a precursor is a product of SPPS, which is partly or fully protected at its side chains and conjugated to its resin, i.e., solid-phase conjugated.

Further, the present invention provides a solid-phase conjugated glucagon-like precursor peptide (in particular a precursor peptide of Liraglutide), wherein at least the side chains of Glu, Asp, and Lys carry protecting groups, and wherein at least one 0-isoacyl peptide bond to serine or threonine is present and/or at least one pseudoproline is present at a position selected from Gly$^4$-Thr$^5$, Phe$^6$-Thr$^7$, Thr$^7$-Ser$^8$, Val$^{10}$-Ser$^{11}$ or Ser$^{11}$-Ser$^{12}$ and/or at least one peptide bond is N-alkylated by 2-hydroxy-4-methoxybenzyl (Hmb) or 2,4-dimethoxybenzyl (Dmb) moieties.

Particularly preferably, the precursor peptide comprises at least one pseudoproline dipeptide selected, e.g., from Fmoc-Gly-Thr(Psi(Me,Me)pro)-OH, Fmoc-Thr(tBu)-Ser(Psi(Me,Me)pro)-OH, Fmoc-Val-Ser(Psi(Me,Me)pro)-OH, Fmoc-Ser(tBu)-Ser(Psi(Me,Me)pro)-OH and in particular Fmoc-Phe-Thr(Psi(Me,Me)pro)-OH.

The present invention further relates to a method of preparing a peptide of formula I, wherein said peptide is obtained from the above precursor peptide conjugated to a resin (i.e., solid-phase bound, side-chain protected Liraglutide derivative) by incubation with a TFA-containing cleavage composition. This incubation may be carried out as described above.

The present invention also refers to a Liraglutide peptide as obtainable from a precursor peptide cleaved off from a resin as described before.

Moreover, the present invention provides a pharmaceutical composition comprising a glucagon-like peptide produced according to the methods of the present invention, or comprising a glucagon-like peptide produced by cleavage from the solid-phase conjugated glucagon-like peptide of the present invention. Therefore, a further aspect of the present invention refers to a pharmaceutical composition comprising:

(A) a Liraglutide peptide obtainable from a method according to the present invention or a Liraglutide peptide obtainable from cleaving the precursor peptide according to the present invention off its solid phase, and (B) a pharmaceutically acceptable carrier.

A pharmaceutically acceptable carrier may be any additive or composition of additives known for this purpose. Such additive may exemplarily be a non-toxic solvent such as, e.g., water, dimethyl sulfoxide (DMSO), ethanol, vegetable oil, paraffin oil or combinations thereof. Furthermore, a carrier may contain one or more detergents, one or more foaming agents (e.g., sodium lauryl sulfate (SLS)/sodium doceyl sulfate (SDS)), one or more coloring agents (e.g., TiO$_2$, food coloring), one or more vitamins, one or more salts (e.g., sodium, potassium, calcium, zinc salts), one or more humectants (e.g., sorbitol, glycerol, mannitol, propylenglycol, polydextrose), one or more enzymes, one or more preserving agents (e.g., benzoic acid, methylparabene), one or more texturing agents (e.g., carboxymethyl cellulose (CMC), polyethylene glycol (PEG), sorbitol), one or more emulsifiers, one or more bulking agents, one or more glacing agents, one or more separating agents, one or more antioxidants, one or more herbal and plant extracts, one or more stabilizing agents, one or more polymers (e.g., hydroxypropyl methacrylamide (HPMA), polyethylene imine (PEI), carboxymethyl cellulose (CMC), polyethylene glycol (PEG)), one or more uptake mediators (e.g., polyethylene imine (PEI), dimethyl sulfoxide (DMSO), a cell-penetrating peptide (CPP), a protein transduction domain (PTD), an antimicrobial peptide, etc.) one or more antibodies, one or more sweeteners (e.g., sucrose, saccharin Na, stevia), one or more counterstain dyes (e.g., fluorescein, fluorescein derivatives, Cy dyes, an Alexa Fluor dyes, S dyes, rhodamine, quantum dots, etc.), one or more homeopathic ingredients one or more gustatory substances and/or one or more fragrances.

The following Figures and Examples, including the experiments conducted and the results achieved, together with the claims are provided for illustrative purposes.

EXAMPLES

Example 1: Solid Phase Peptide Synthesis of Glucagon-Like Peptides

Stepwise Fmoc-SPPS of Liraglutide was performed on a 100-200 or 200-400 mesh H-Gly-2-chlorotrityl resin (Bachem no. 4092098 or 4026823) using the standard Fmoc amino acid derivatives Fmoc-Ala-OH, Fmoc-Arg(Pbf)-OH, Fmoc-Asp(OtBu)-OH, Fmoc-Asp(OMpe)-OH, Fmoc-Gly-OH, Fmoc-Gln(Trt)-OH, Fmoc-Glu(OtBu)-OH, Boc-His(Boc)-OH, Fmoc-His(1-Trt)-OH Fmoc-Ile-OH, Fmoc-Leu-OH, Fmoc-Phe-OH, Fmoc-Ser(tBu)-OH, Fmoc-Thr(tBu)-OH, Fmoc-Trp(Boc)-OH, Fmoc-Tyr(tBu)-OH, and Fmoc-Val-OH, as well as the previously described building block Fmoc-Lys($N^\varepsilon$-(γ-glutamyl(OtBu)-($N^\alpha$-hexadecanoyl))) (=Fmoc-Lys(palmitoyl-Glu-OtBu)-OH, see WO 2013/171135) and at least one pseudoproline dipeptide selected from Fmoc-Gly-Thr(Psi(Me,Me)pro)-OH, Fmoc-Phe-Thr(Psi(Me,Me)pro)-OH, Fmoc-Thr(tBu)-Ser(Psi(Me,Me)pro)-OH, Fmoc-Val-Ser(Psi(Me,Me)pro)-OH, and Fmoc-Ser(tBu)-Ser(Psi(Me,Me)pro)-OH. Coupling reactions were executed either with DIC/OXYMAPURE® (cyano-hydroxyimino-acetic acid ethyl ester), TBTU/DIPEA or DEPBT/DIPEA with appropriate coupling (1.5-24.0 h) and Fmoc deprotection (0.5-4.0 h) times.

When desired, 20% piperidine in NMP was used instead of 20% piperidine in DMF to enhance deprotection rates. After coupling steps, an acetylation was optionally performed using acetic anhydride. DMF and IPA were used as solvents for the washing steps after acetylation or Fmoc deprotection. Crude Liraglutide was typically obtained after cleavage and precipitation with a U-HPLC purity of about 50%.

Alternatively, a stepwise protocol was carried out involving the use of Fmoc-Lys(Boc-Glu-OtBu)-OH as a building block and subsequent palmitoylation of the purified peptide as follows.

Stepwise Fmoc SPPS of a fully protected peptide of the primary amino acid sequence:

```
His-Ala-Glu-Gly-Thr-Phe-Thr-Ser-Asp-Val-Ser-Ser-
Tyr-Leu-Glu-Gly-Gln-Ala-Ala-Lys(Boc-Glu-OtBu)-Glu-
Phe-Ile-Ala-Trp-Leu-Val-Arg-Gly-Arg-Gly-[resin]
``` was carried out on a automated synthesizer using a H-Gly-2-chlorotrityl resin. Coupling reactions were carried out using the respective standard Fmoc amino acid derivative, DIC/OXYMAPURE® (cyano-hydroxyimino-acetic acid ethyl ester) or TBTU/DIPEA as coupling reagents and DMF as a solvent. As an exception, the coupling of Boc-His(Boc)-OH was carried out using DEPBT/DIPEA in DMF. The coupling time varied between 1.5 h and 4 h. The introduction of the Fmoc-Lys(Boc-Glu-OtBu)-OH building block was performed manually (DIC/OXYMAPURE® (cyano-hydroxyimino-acetic acid ethyl ester), 4 h coupling time) whereas the rest of the synthesis was conducted via fully automated peptide synthesis. Fmoc deprotection was performed using a solution of 20% piperidine in DMF (v/v). Deprotection time varied between 15 up to 90 min. After each coupling, an systematic capping step was performed using acetic anhydride.

DMF and/or IPA were used as solvents for the washing steps after Fmoc deprotection and acetylation. The peptide was cleaved from the solid support with concomitant removal of all the side chain protecting groups by incubation with a cleavage composition consisting of TFA/$H_2O$/EDT (90:5:5) v/v/v for 2.5 h, followed by precipitation. The resulting crude material was subjected to a two dimensional preparative reversed phase HPLC using C8-bonded silica as a stationary phase, a TEAP eluent system in the first, and a TFA eluent system in the second dimension. The purified precursor peptide had an U-HPLC purity of typically 95% and was reacted with N-succinimidyl palmitate in aqueous solution comprising 66% THF. The resultant product was precipitated by evaporation of the solvent, re-dissolved by the addition of 50% AcOH in 10% ACN/$H_2O$ and filtered.

Example 2: Precipitation of Glucagon-Like Peptides from the Cleavage Composition General Procedure:

Peptide resin (5 g) was suspended in 50 mL of cleavage composition and stirred for 3 h at RT. The resin was then filtered off and washed with TFA (2×3.5 mL). The cleavage composition and washing fractions were pooled. 570 mL of the respective anti-solvent was added to initiate precipitation. The resulting suspension was stirred for a further 2 h before separating the peptide precipitate by the use of either a filter funnel or a standard pressurized filter equipment ("pocket filter"). Filtration time and gross yield based on peptide resin were determined. The precipitate was washed with the respective ether (3×15 mL) and dried under vacuum at RT to yield the crude peptide.

Alternatively, peptide resin (3 g) was suspended in 30 mL cleavage composition and stirred for 3 h at RT. The resin was then filtered off and washed with TFA (2×2.1 mL). The cleavage composition and washing fractions were pooled. The solution was added to 342 mL of anti-solvent to initiate precipitation. The resulting suspension was stirred for a further 2 h before separating the peptide precipitate by the use of either a filter funnel or a standard pressurized filter equipment ("pocket filter"). Filtration time and gross yield based on peptide resin were determined. The precipitate was washed with the respective ether (3×18 mL) and dried under vacuum at RT to yield the crude peptide.

Results:

The dried peptide precipitate was analyzed for purity and TFA content by analytical reversed phase UHPLC, and the aggregate content was determined by analytical size exclusion UHPLC. The appearance/stickiness of the precipitate was assessed by visual inspection.

As shown in Table 2, it was found that precipitation with mixtures of IPE/ACN in a range of 1:3-1:10 not only resulted in acceptable yields and filtration times but also improved the precipitate's purity as compared to pure ether anti-solvents (compare lines 5-7 with lines 1-3).

The purity could further be improved to 63.1% when the anti-solvent was not pre-mixed, but divided in an ACN part and an IRE part and said parts were contacted subsequently with the peptide solution (data not shown). To further facilitate the comparison of the various precipitation methods, a performance score P was calculated as P $P = P_{filtration\ time} \times P_{purity} \times P_{yield} \times P_{appearance} \times P_{aggregate\ content}$. As each sub-score ranged from 1-3, the maximal performance score is 243, the minimal score is 1. Also if assessed by this metric, mixtures of IPE/ACN were found to be clearly advantageous compared to the other anti-solvents tested.

TABLE 2

Precipitation of Liraglutide from TFA/water/EDT/TIPS cleavage composit.

| Experiment No. | Performance Score | Anti-solvent | Mode | Yield [%] | Filtration Time [min] | HPLC Purity [%] | Appearance |
|---|---|---|---|---|---|---|---|
| EOP18a | 54 (3 × 3 × 3 × 2 × 1) | IPE | Classic | 44 | 01:36 | 55.85 | Precipitate slightly sticky |
| EOP19a | 18 (3 × 2 × 3 × 1 × 1) | Et$_2$O | classic | 42 | 00:47 | 52.52 | precipitate sticky |
| EOP20a | 72 (3 × 2 × 3 × 2 × 2) | MTBE | classic | 43 | 01:18 | 52.2 | precipitate slightly sticky |
| EOP5i | 18 (3 × 3 × 1 × 1 × 2) | IPE/ACN 1:1 | classic | 1 | 00:31 | 74.29 | Very fine particles, small sticky lumps |
| EOP23a | 108 (3 × 3 × 2 × 3 × 2) | IPE/ACN 3:1 | classic | 36 | 1:47 | 60.52 | Precipitate not sticky |
| EOP22a | 162 (3 × 3 × 3 × 3 × 2) | IPE/ACN 5:1 | classic | 39 | 01:58 | 56.08 | Precipitate not sticky |
| EOP21a | 18 (2 × 3 × 3 × 1 × 1) | IPE/ACN 10:1 | classic | 42 | 05:13 | 57.12 | Precipitate sticky |
| EOP3a | 36 (1 × 3 × 2 × 3 × 2) | IPE/hexane 1:2 | inverse | 34 | 70:00:00 | 68.1 | Fine precipitate |
| EOP28a | 1 (1 × 1 × 1 × 1 × 1) | IPE/hexane 1:2 | classic | n/a | n/a | n/a | Oiling out |
| EOP24a | 36 (3 × 2 × 3 × 1 × 2) | IPE/hexane 5:1 | classic | 41 | 01:00 | 52.53 | sticky |

Example 3: Composition of Peptide Solution

A further experiment was carried out as in Example 2 above, but using a cleavage composition composed of TFA/thioanisole/anisole/EDT (90:5:3:2) v/v/v/v, which is disclosed in EP-A 2 757 107 for the preparation of Liraglutide.

The observed performance score of 108 (3×2×3×3×2) illustrates that the advantageous effect of the IPE/ACN anti-solvent is not limited to one specific peptide containing solution.

Example 4: Precipitation Temperature

Further experiments were carried out as in Example 2 above to analyze the preferred temperature range for the precipitation.

TABLE 3

Precipitation temperature

| EXPERIMENT No. | Anti-Solvent | Temperature [° C.] | Yield [%] | Filtration Time [min:sec] | HPLC Purity [%] | Appearance |
|---|---|---|---|---|---|---|
| EOP6a | IPE/ACN 3:1 | 0 to 6° C. | 28 | 5:55 | 64.84 | Precipitate not sticky |
| EOP7a | IPE/ACN 3:1 | −10 to −3° C. | 37 | 4:51 | 60.52 | Precipitate not sticky |
| EOP8a | IPE/ACN 3:1 | 10 to 17° C. | 32 | 3:11 | 60.52 | Precipitate not sticky |

Example 5: Comparative Example

Liraglutide was cleaved off the resin by incubation with TFA/thioanisole/anisole/EDT (90:5:3:2) v/v/v/v and precipitated using ice-cooled diethyl ether as is described in EP-A 2 757 107. The precipitate was analyzed as in Example 2 above.

TABLE 4

Performance of comparative precipitation protocol

| EXPERIMENT No. | Performance Score | Yield [%] | Filtration time [min] | HPLC Purity [%] | Appearance |
|---|---|---|---|---|---|
| EOP26a | 18 (2 × 1 × 3 × 3 × 1) | 38 | 22:30 | 44.89 | Fine Precipitate |

Representative suspensions obtained from Example 5 (Experiment No. EOP26a), and EOP22a of Example 2 were analyzed by Focused Beam Reflectance Measurement (FBRM) technology using a ParticleTrack G600L device. FBRM technology allows determination of the particle size distribution after precipitation based on the detection of backscattered laser light.

Figure 2:
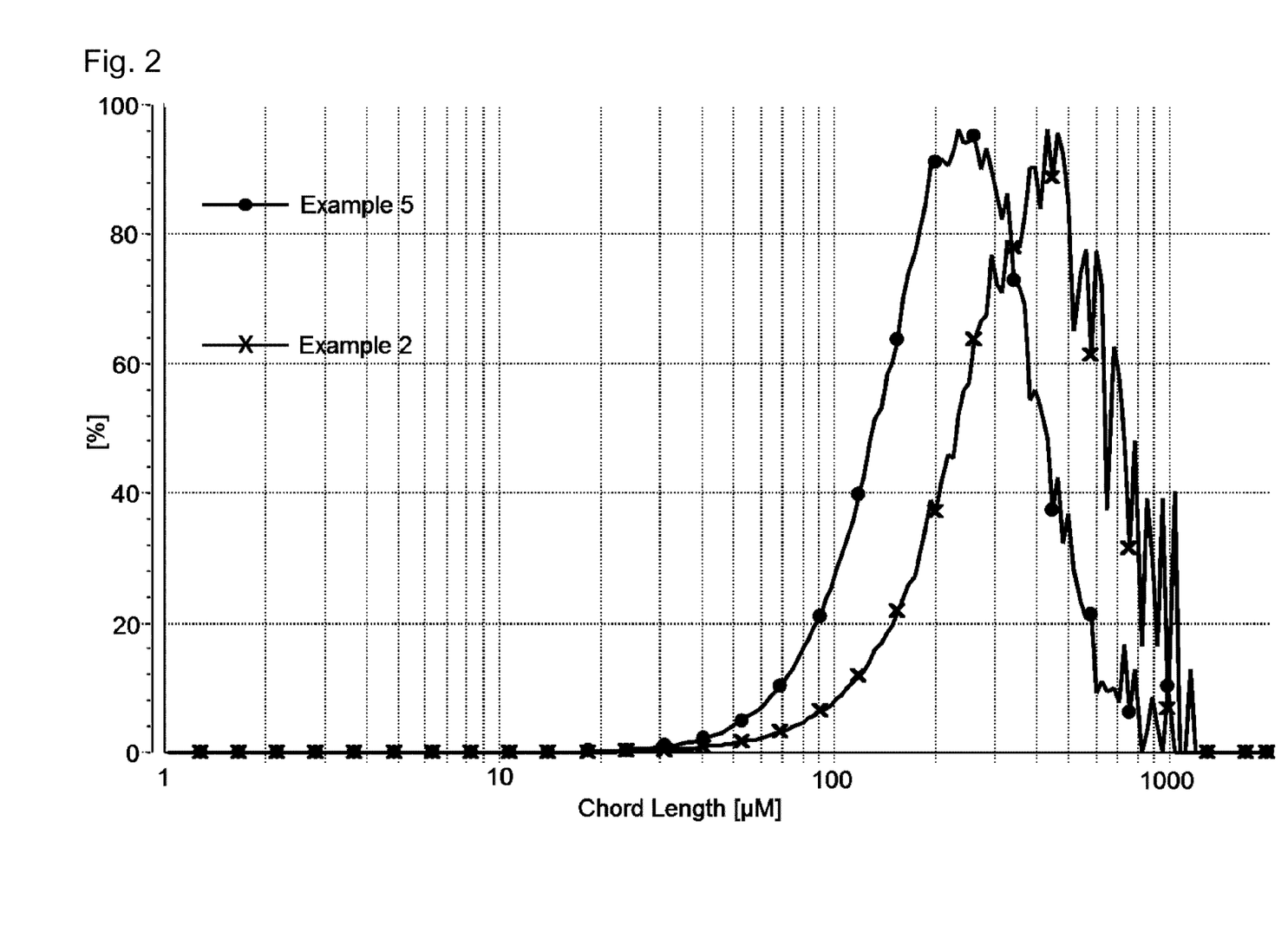
FIG. 2 shows the particle size distribution of peptide precipitates as measured by FBRM technology (conducted on the following device: ParticleTrack G600L, Mettler Toledo, Settings: Macro V1.1.11, cube weight, normalized, mean (cube weight)). The chord length is the distance across each particle as calculated based on scan speed and the number and duration of distinct pulses of backscattered light. The percentage given relates to the number of detected particles and is normalized such that the maximal number of particles of a given size within one scan is 100%. Herein, the precipitate EOP26a of Example 5 (anti-solvent: diethyl ether mean particle size: 261 μm) is compared with the precipitate EOP22a of Example 2 (anti-solvent: IPE/ACN mean particle size: 422 μm)

As shown in FIG. 2 it was found that the precipitate of the present invention was characterized by a shift in its particle size distribution to larger size. The mean particle size was 422 μm for the precipitate produced according to the present invention as compared to a mean particle size of 261 μm for the precipitate produced according to the protocol of EP-A 2 757 107. This translates to a significant difference in filtration rates with much faster filtration obtained by the present invention. Hence, it is concluded that the precipitates obtained according to the present invention differ from those disclosed in the prior art not only by their improved purity and macroscopic properties, but also in terms of their size distribution.

Example 6: Composition of Peptide Precipitate

A crude liraglutide peptide precipitate obtained as in Example 2 above was analyzed by analytical reversed phase UHPLC and mass spectrometry for truncated Liraglutide variants. N-terminally truncated Liraglutide variants could be

---

The invention claimed is:

1. A method for preparing a Liraglutide peptide or a salt thereof, comprising:
   (i) providing a solution S comprising a peptide of formula I:

His-Ala-Glu-Gly-Thr-Phe-Thr-Ser-Asp-Val-Ser-Ser-
   Tyr-Leu-Glu-Gly-Gln-Ala-Ala-B$^1$-Glu-Phe-Ile-Ala-
   Trp-Leu-Val-Arg-Gly-Arg-Gly, wherein B$^1$ is Lys(palmitoyl-Glu-OH) or Lys(H-Glu-OH);
   (ii) precipitation of the peptide of step (i) by mixing solution S with an anti-solvent comprising at least 50% (v/v) of diisopropyl ether and acetonitrile, wherein the volume ratio (diisopropyl ether:acetonitrile) is in the range of from (3:1) to (5:1); and
   (iii) isolating the precipitate obtained from step (ii).

2. The method according to claim 1, wherein step (i) comprises:
   (i-a) providing a precursor peptide conjugated to a solid phase:

His-Ala-Glu-Gly-Thr-Phe-Thr-Ser-Asp-Val-Ser-Ser-
   Tyr-Leu-Glu-Gly-Gln-Ala-Ala-B$^2$-Glu-Phe-Ile-Ala-
   Trp-Leu-Val-Arg-Gly-Arg-Gly-[resin], wherein B$^2$ is Lys (palmitoyl-Glu-OR$_1$) or B$^2$ is Lys (R$_2$-Glu-OR$_1$), with R$_1$ being a carboxylic acid protecting group and R$_2$ being an amino protecting group; and wherein at least the side chains of Glu, Asp, and Lys bear protecting groups; and
   (i-b) cleaving the precursor peptide off the resin.

3. The method according to claim 2, wherein step (i-a) comprises Fmoc-based Solid Phase Peptide Synthesis using suitably protected amino acid derivatives or dipeptide derivatives, wherein said protected amino acid derivatives or dipeptide derivatives are activated by one or more coupling reagent/additive mixtures selected for each step independently from the group consisting of:
   (A) (benzotriazolyl)tetramethyluronium tetrafluoroborate (TBTU)/diisopropylethylamine (DIPEA);
   (B) diisopropylcarbodiimide (DIC)/cyano-hydroxyiminoacetic acid ethyl ester;
   (C) 3-(diethoxy-phosphoryloxy)-3H-benzo[d][1,2,3]triazin-4-one (DEPBT)/DIPEA; and
   (D) DIC/hydroxybenzotriazole (HOBt).

4. The method according to claim 2, wherein one or more pseudoproline dipeptides are introduced at a position selected from the group consisting of Gly$^4$-Thr$^5$, Phe$^6$-Thr$^7$, Thr$^7$-Ser$^8$, Val$^{10}$-Ser$^{11}$, and Ser$^{11}$-Ser$^{12}$ of the peptide of formula I.

5. The method according to claim 2, wherein the N-terminal histidine moiety is introduced into the precursor peptide conjugated to the solid phase using an amino acid derivative selected from the group consisting of Boc-His (Boc)-OH, Boc-His(1-Trt)-OH, and Fmoc-His(1-Trt)-OH and the coupling reagent/additive mixture DEPBT/DIPEA.

6. The method according to claim 3, wherein the Fmoc protecting group is cleaved off the growing peptide chain conjugated to the solid phase using a mixture selected from the group consisting of 5-50% (v/v) piperidine or 4-methyl piperidine in N,N-dimethylformamide (DMF), 5-50% (v/v) piperidine or 4-methyl piperidine in N-methylpyrrolidone (NMP), 1-5% (v/v) diazabicyclo[5.4.0]undec-7-ene (DBU) in DMF, and 50% (v/v) morpholine in DMF.

7. The method according to claim 1, further comprising a step of reacting an activated ester of palmitic acid, with the Lys(H-Glu-OH) moiety of the peptide of formula I or with a Lys(H-Glu-OR$_1$) moiety obtainable by cleaving off the amino protecting group R$_2$ from the precursor peptide provided in step (i-a).

8. The method according to claim 1, wherein the solution S obtained from step (i) further comprises trifluoroacetic acid (TFA) and one or more scavengers.

9. The method according to claim 1, wherein the anti-solvent used in step (ii) comprises at least 75% (v/v), of a mixture M of diisopropyl ether and acetonitrile, and wherein the volume ratio (diisopropyl ether:acetonitrile) in said mixture M is in the range of from (3:1) to (5:1).

10. The method according to claim 1, wherein step (ii) comprises mixing the anti-solvent with solution S obtained from step (i) by:
    (ii-a) pre-mixing diisopropyl ether and acetonitrile before mixing it with the solution S obtained from step (i); or
    (ii-b) first mixing diisopropyl ether with the solution S obtained from step (i) and subsequently mixing acetonitrile with the mixture comprising solution S and diisopropyl ether; or
    (ii-c) first mixing acetonitrile with the solution S obtained from step (i) and subsequently mixing diisopropyl ether with the mixture comprising solution S and acetonitrile.

11. The method according to claim 1, wherein step (ii) is carried out at a temperature in the range of −5° C. to 10° C.

12. The method according to claim 1, wherein in step (iii), the precipitate obtained from step (ii) is isolated by filtration, centrifugation, or a combination of filtration and centrifugation.

* * * * *

SEQUENCE LISTING

```
<160> NUMBER OF SEQ ID NOS: 7

<210> SEQ ID NO 1
<211> LENGTH: 28
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn
            20                  25

<210> SEQ ID NO 2
<211> LENGTH: 33
<212> TYPE: PRT
<213> ORGANISM: Homo sapiens

<400> SEQUENCE: 2

His Ala Asp Gly Ser Phe Ser Asp Glu Met Asn Thr Ile Leu Asp Asn
1               5                   10                  15

Leu Ala Ala Arg Asp Phe Ile Asn Trp Leu Ile Gln Thr Lys Ile Thr
            20                  25                  30

Asp

<210> SEQ ID NO 3
<211> LENGTH: 31
<212> TYPE: PRT
<213> ORGANISM: Homo sapiens

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

```
<210> SEQ ID NO 4
<211> LENGTH: 31
<212> TYPE: PRT
<213> ORGANISM: Artificial Sequence
<220> FEATURE:
<223> OTHER INFORMATION: glucagon-like peptide liraglutide polypeptide

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 5
<211> LENGTH: 39
<212> TYPE: PRT
<213> ORGANISM: Homo sapiens

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: glucagon-like peptide exenatide

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 7
<211> LENGTH: 44
<212> TYPE: PRT
<213> ORGANISM: Artificial Sequence
<220> FEATURE:
<223> OTHER INFORMATION: glucagon-like peptide lixisenatide

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40
```